(12) United States Patent
Du et al.

(10) Patent No.: US 11,903,757 B2
(45) Date of Patent: Feb. 20, 2024

(54) METHOD AND SYSTEM FOR ULTRASONIC FLUID SPECTRAL DOPPLER IMAGING

(71) Applicant: Shenzhen Mindray Bio-Medical Electronics Co., Ltd., Shenzhen (CN)

(72) Inventors: Yigang Du, Shenzhen (CN); Shuangshuang Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 88 days.

(21) Appl. No.: 17/503,969

(22) Filed: Oct. 18, 2021

(65) Prior Publication Data

US 2022/0031279 A1 Feb. 3, 2022

Related U.S. Application Data

(63) Continuation of application No. 16/232,262, filed on Dec. 26, 2018, now Pat. No. 11,259,773, which is a (Continued)

(51) Int. Cl.
*A61B 8/06* (2006.01)
*A61B 8/14* (2006.01)
(Continued)

(52) U.S. Cl.
CPC .............. *A61B 8/06* (2013.01); *A61B 8/14* (2013.01); *A61B 8/463* (2013.01); *A61B 8/488* (2013.01); *A61B 8/5246* (2013.01); *G01F 1/663* (2013.01)

(58) Field of Classification Search
CPC .. A61B 8/06; A61B 8/14; A61B 8/463; A61B 8/488; A61B 8/5246; G01F 1/663
See application file for complete search history.

(56) References Cited

U.S. PATENT DOCUMENTS 5,243,987 A * 9/1993 Shiba ................... G01N 29/032
600/463
5,322,066 A  6/1994 Miyataka
(Continued)

FOREIGN PATENT DOCUMENTS

CN    102421372 A    4/2012
CN    102551791 A    7/2012
(Continued)

OTHER PUBLICATIONS

United States Patent and Trademark Office, U.S. Appl. No. 17/504,001, Office Action dated Apr. 5, 2023, 11 pages.

*Primary Examiner* — Oommen Jacob
(74) *Attorney, Agent, or Firm* — Kory D. Christensen

(57) ABSTRACT

A method and system for ultrasonic fluid spectral Doppler imaging are disclosed. The system comprises: a transmission circuit for transmitting an ultrasonic beam to a detection object; a receiving circuit and a beam synthesis module for receiving an echo of the ultrasonic beam and obtaining an ultrasonic echo signal; an image processing module for obtaining an ultrasonic fluid flow state image of a region of interest in the detection object according to the ultrasonic echo signal, identifying a sampling position in the region of interest, respectively obtaining a Doppler spectrogram corresponding to each sampling position according to the ultrasonic echo signal, and generating position displaying marks for characterizing the sampling positions; and a display for displaying the position displaying marks in the ultrasonic fluid flow state image, and displaying the obtained Doppler spectrogram. The system may simultaneously display spectra of multiple locations on a same time axis.

8 Claims, 11 Drawing Sheets

Related U.S. Application Data continuation of application No. PCT/CN2016/087927, filed on Jun. 30, 2016.

(51) Int. Cl.
   *A61B 8/00* (2006.01)
   *A61B 8/08* (2006.01)
   *G01F 1/663* (2022.01)

(56) References Cited

U.S. PATENT DOCUMENTS

| | | |
|---|---|---|
| 5,555,886 A | 9/1996 | Weng et al. |
| 5,846,203 A | 12/1998 | Koo |
| 6,464,637 B1 | 10/2002 | Criton et al. |
| 6,527,720 B1 | 3/2003 | Ustuner |
| 7,753,850 B2 | 7/2010 | Averkiou |
| 9,060,669 B1 | 6/2015 | Mo |
| 9,204,858 B2 * | 12/2015 | Pelissier ............ A61B 8/0891 |
| 10,335,113 B2 | 7/2019 | Yu |
| 10,342,515 B2 * | 7/2019 | Loupas ............ G01S 15/8988 |
| 10,835,200 B2 * | 11/2020 | Shibata ............ A61B 8/54 |
| 2003/0163044 A1 * | 8/2003 | Heimdal ............ A61B 8/485 |
| | | 600/437 |
| 2006/0052698 A1 * | 3/2006 | Loupas ............ A61B 8/483 |
| | | 600/437 |
| 2006/0106309 A1 | 5/2006 | Liu |
| 2007/0167790 A1 | 7/2007 | Kim |
| 2007/0167797 A1 | 7/2007 | Averkiou |
| 2009/0149755 A1 | 6/2009 | Ahn et al. |
| 2010/0022884 A1 * | 1/2010 | Ustuner ............ A61B 8/461 |
| | | 600/453 |
| 2012/0116218 A1 | 5/2012 | Martin |
| 2013/0079680 A1 | 3/2013 | Stein |
| 2013/0172754 A1 | 7/2013 | Kim |
| 2014/0276072 A1 * | 9/2014 | Martins ............ A61B 8/463 |
| | | 600/454 |
| 2015/0141824 A1 * | 5/2015 | You ............ A61B 8/06 |
| | | 600/441 |
| 2016/0183918 A1 * | 6/2016 | Yang ............ A61B 8/56 |
| | | 600/443 |
| 2018/0146952 A1 | 5/2018 | Du |
| 2019/0314000 A1 | 10/2019 | Du |
| 2022/0031279 A1 * | 2/2022 | Du ............ A61B 8/488 |
| 2022/0031280 A1 * | 2/2022 | Du ............ A61B 8/5246 |

FOREIGN PATENT DOCUMENTS

| | | |
|---|---|---|
| CN | 1 031 81 782 A | 7/2013 |
| CN | 104684488 A | 6/2015 |
| CN | 105167802 A | 12/2015 |
| WO | WO 01/71376 | 9/2001 |

* cited by examiner

METHOD AND SYSTEM FOR ULTRASONIC FLUID SPECTRAL DOPPLER IMAGING

CROSS-REFERENCE TO RELATED APPLICATIONS

This application is a continuation of U.S. patent application Ser. No. 16/232,262, filed Dec. 26, 2018, for "METHOD AND SYSTEM FOR ULTRASONIC FLUID SPECTRAL DOPPLER IMAGING," which is a continuation of PCT Application No. PCT/CN2016/087927, filed Jun. 30, 2016, for "METHOD AND SYSTEM FOR ULTRASONIC FLUID SPECTRAL DOPPLER IMAGING," which is incorporated herein by reference.

TECHNICAL FIELD

The present disclosure relates to medical diagnostic equipment and particularly to a method and system for ultrasonic flow spectral Doppler imaging.

BACKGROUND

An ultrasonic flow imaging system can examine objects containing blood flow body flows, and the like, such as moving organs, blood vessels, etc. A focused wave can be transmitted to the examination target, and echo signals can be obtained. Processes such as beam-forming, etc. can be performed on the echo signals to obtain an ultrasonic image, which can be displayed on a display. The ultrasonic image provides important parameter references for a doctor to diagnose and therefore is widely used in clinical examinations.

There may be different flow patterns in one object at the same time. For example, at the carotid bifurcation, even a healthy person may have vortexes at the carotid sinus during systole. In the case of atherosclerosis or there being plaque at the carotid sinus, there may be large vortexes, as well as turbulence and other different situations.

Therefore, it is desired to provide a more comprehensive diagnosis basis for the doctor by using the ultrasonic flow imaging system to present the measurement results wholly and comprehensively.

SUMMARY

In one embodiment, a new imaging method may be provided to present more measurement results for doctors.

In one embodiment, an ultrasonic flow spectral Doppler imaging method may be provided, which may include: transmitting an ultrasonic beam to an examination object; receiving echoes of the ultrasonic beam to obtain an ultrasonic echo signal; obtaining an ultrasonic flow state image of a region of interest in the examination object according to the ultrasonic echo signal; determining sampling positions in the region of interest, where the number of the sampling positions is greater than or equal to two; obtaining a Doppler spectrum corresponding to each sampling position according to the ultrasonic echo signal; displaying position displaying marks on the ultrasonic flow state image, where one position displaying mark correspondingly marks one sampling position; and displaying the obtained Doppler spectrums.

In one embodiment, an ultrasonic flow spectrum Doppler imaging method may be provided, which may include: transmitting an ultrasonic beam to an examination object; receiving echoes of the ultrasonic beam to obtain an ultrasonic echo signal; obtaining an ultrasonic image of a region of interest in the examination object according to the ultrasonic echo signal; determining a sampling position in the region of interest; obtaining a Doppler spectrum corresponding to the sampling position according to the ultrasonic echo signal; drawing a closed box at a position corresponding to the sampling position in the ultrasonic image and drawing an angle correction line associated with the box to form a position displaying mark representing the sampling position; displaying the position displaying mark in an ultrasonic blood flow projection image; and displaying the obtained Doppler spectrum.

In one embodiment, an ultrasonic flow spectrum Doppler imaging method may be provided, which may include: transmitting an ultrasonic beam to an examination object; receiving echoes of the ultrasonic beam to obtain an ultrasonic echo signal; obtaining an ultrasonic image of a region of interest in the examination object according to the ultrasonic echo signal; determining a first sampling position in the region of interest and obtaining a first Doppler spectrum corresponding to the first sampling position according to the ultrasonic echo signal; determining a second sampling position in the region of interest and obtaining a second Doppler spectrum corresponding to the second sampling position according to the ultrasonic echo signal; evaluating a difference between the first Doppler spectrum and the second Doppler spectrum; and outputting the difference.

In one embodiment, an ultrasonic flow spectrum Doppler imaging system may be provided, which may include: a transmitting circuit which transmits an ultrasonic beam to an examination object; a receiving circuit and a beam-former which receives echoes of the ultrasonic beam to obtain an ultrasonic echo signal; an image processor which is configured to obtain an ultrasonic flow state image of a region of interest in the examination object according to the ultrasonic echo signal, determine sampling positions in the region of interest the number of which is more than or equal to two, obtain a Doppler spectrum corresponding to each sampling position according to the ultrasonic echo signal, and generate position displaying marks representing the sampling positions, wherein one position displaying mark corresponds to one sampling position; and a display which displays the position displaying marks in the ultrasonic flow state image and displays the obtained Doppler spectrums.

In one embodiment, an ultrasonic flow spectrum Doppler imaging system may be provided, which may include: a transmitting circuit which transmits an ultrasonic beam to an examination object; a receiving circuit and a beam-former which receives echoes of the ultrasonic beam to obtain an ultrasonic echo signal; an image processor which is configured to obtain an ultrasonic image of a region of interest in the examination object according to the ultrasonic echo signal, determine a sampling position in the region of interest, obtain a Doppler spectrum corresponding the sampling position according to the ultrasonic echo signal, and draw a closed box at a position corresponding to the sampling position in the ultrasonic image and draw an angle correction line associated with the box to form a position displaying marker representing the sampling position; and a display which displays the position displaying mark in the ultrasonic blood flow projection image and displays the obtained Doppler spectrum.

In one embodiment, an ultrasonic flow spectrum Doppler imaging system may be provided, which may include: a transmitting circuit which transmits an ultrasonic beam to an examination object; a receiving circuit and a beam-former which receives echoes of the ultrasonic beam to obtain an ultrasonic echo signal; an image processor which obtains an ultrasonic image of a region of interest in the examination object according to the ultrasonic echo signal, determines a first sampling position in the region of interest and obtains a first Doppler spectrum corresponding to the first sampling position according to the ultrasonic echo signal, determines a second sampling position in the region of interest and obtains a second Doppler spectrum corresponding to the second sampling position according to the ultrasonic echo signal, and evaluates a difference between the first Doppler spectrum and the second Doppler spectrum; and a display and/or an audio player which outputs the difference.

BRIEF DESCRIPTION OF THE DRAWINGS

In order to illustrate the embodiments of the present disclosure or the technical solutions in the prior art more clearly, the drawings used in the embodiments or the description of the prior art will be briefly described below. Obviously, the drawings in the following description are only certain embodiments of the present disclosure, and other drawings can be obtained by those skilled in the art according to these drawings without any creative work.

DETAILED DESCRIPTION

The present disclosure will be described in detail below with reference to the accompanying drawings.

Figure 1:
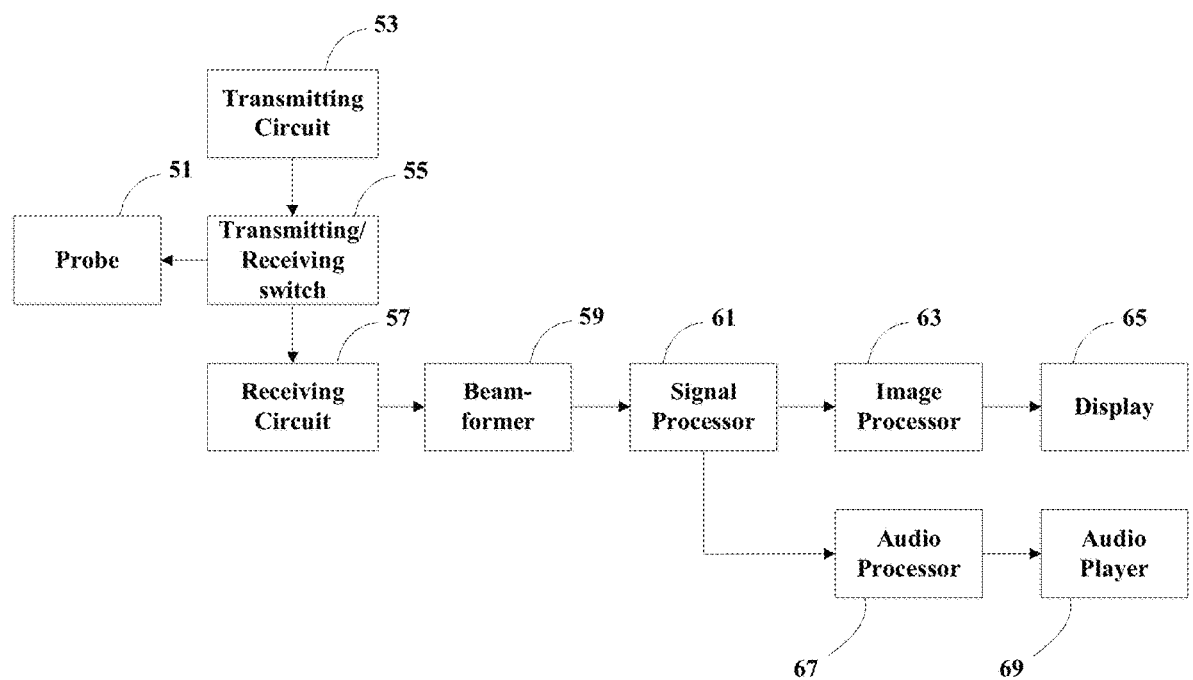
FIG. 1 is a schematic block diagram of one embodiment of an ultrasonic flow spectral Doppler imaging system of the present disclosure.

FIG. 1 is a block diagram showing the structure of one embodiment of an ultrasonic flow spectral Doppler imaging system. As shown in FIG. 1, the ultrasonic flow spectrum Doppler imaging system 50 mainly includes a probe 51, a transmitting circuit 53, a transmitting/receiving switch 55, a receiving circuit 57, a beam-former 59, a signal processor 61, and an image processor 63 and a display 65. In addition, an audio processor 67 and an audio player 69 may also be included according to actual needs.

During the ultrasonic imaging, the transmitting circuit 53 may transmit delay-focused transmission pulses having a certain amplitudes and polarities to the probe 51 through the transmitting/receiving switch 55. The probe 51 may be excited by the transmission pulse to transmit an ultrasonic beam to an examination object containing a flow (for example, a blood vessel existing in an organ, a tissue, or the like in a human body or an animal body, or another vessel containing a flow in the living body, not shown), receive ultrasonic echoes carrying flow information reflected from the target area after a certain delay, and convert the ultrasonic echoes into electrical signals. The flow may include flows present in tissues such as blood vessels, lymphatic systems, etc. in the human or animal body, or flowing flows present in other vessels in the human or animal body, not shown.

The receiving circuit 57 may receive the electrical signals generated by the probe 51 thereby obtaining ultrasonic echo signals, and send the ultrasonic echo signals to the beam-former 59. The beam-former 59 may perform processing such as focus delay, weighting and channel summation, etc. on the ultrasonic echo signals, and then send the ultrasonic echo signals to the signal processor 61 for related signal processing to obtain flow signals carrying flow motion information.

The ultrasonic echo signals processed by the signal processor 61 may be sent to the image processor 63. The image processor 63 may perform different processing on the signals according to different imaging modes required by the user to obtain image data of different modes, and perform processing such as logarithmic compression, dynamic range adjustment, digital scan conversion, etc. one the image data to form ultrasonic images of different modes, such as B image, C image, D image, and the like.

The ultrasonic images generated by the image processor 63 may be sent to the display 65 for display.

Alternatively, the ultrasonic echo signals processed by the signal processor 63 may also be sent to the audio processor 67. The audio processor 67 may process the signals to obtain audio data, and then form ultrasonic audio by encoding, decoding, and the like. The ultrasonic audio generated by the audio processor 67 may be sent to the audio player 69 for playback.

In addition, the system may further include a human-machine interface, such as a keyboard, a mouse, a scroll wheel, a touch device for touch screen, and the like. A user input instruction can be obtained through the human-machine interface. The user may operate the system according to the displayed results outputted by the display 65 to generate the instruction to achieve the interaction between the user and the presented results.

The probe 1 may generally include an array of multiple elements. Each time the ultrasonic beam is transmitted, all or a portion of the elements of the probe 1 may participate in the transmission of the ultrasonic beam. At this time, each or each portion of the elements participating in the transmission of the ultrasonic beam may be excited respectively by the transmission pulses and respectively transmit ultrasonic wave. The ultrasonic waves respectively transmitted by the elements may be superimposed during the propagation to form a synthesized ultrasonic beam transmitted to a flow. The direction of the synthesized ultrasonic beam is the transmission direction mentioned herein (which may be equivalent to the direction of propagation of the ultrasonic beam). The elements participating in the transmission of the ultrasonic beam may be excited by the transmitted pulse at the same time. Alternatively, there may be certain time delay between the excitations of the elements participating in the transmission of the ultrasonic beam by the transmitted pulses, thereby changing the propagation direction of the above-described synthesized ultrasonic beam. The superposition mentioned herein may be ordinary summation or weighted summation.

By controlling the delay between the times when the elements participating in the transmission of the ultrasonic beam are excited by the transmission pulses, the ultrasonic waves transmitted respectively by the elements may be superimposed at predetermined positions, so that the intensity of the ultrasonic waves is maximized at the predetermined position, that is, the ultrasonic waves transmitted by the respective elements may be "focused" to the predetermined position. The predetermined position may be referred to as "focus", and the obtained synthesized ultrasonic beam may be a beam focused to the focus, which may be referred to as a focused ultrasonic beam. The focused ultrasonic beam may include a strongly focused ultrasonic beam and a weakly focused ultrasonic beam. When the focus is at a certain position, the ultrasonic beam may be called a strongly focused ultrasonic beam. When the focus is directed to a certain area rather than a specific position, or a ratio of a depth of the focus to a length of the transmit aperture is greater than a certain value, or there are multiple focuses in the scan range, the ultrasonic beam may be called a weakly focused ultrasonic beam.

By controlling the delay between the times when the elements participating in the transmission of the ultrasonic beam are excited by the transmission pulses, it is also possible that the ultrasonic beams transmitted by the respective elements participating in the transmission of the ultrasonic beam are not focused, and not completely diverged, during the propagation, thereby forming a plane wave that is generally planar as a whole. Such unfocused beam is referred to herein as a plane ultrasonic beam. When the ultrasonic waves transmitted by the respective elements participating in the transmission of the ultrasonic beam are diverged during the propagation, a beam which is substantially divergent as a whole is formed. This type of divergent ultrasonic wave is referred to herein as a diverged ultrasonic beam.

In addition to the above-described strongly focused ultrasonic beam, various types of ultrasonic beams, such as the above-mentioned diverged ultrasonic beam, weakly focused ultrasonic beam, plane ultrasonic beam, and virtual source ultrasonic beam, etc., may be collectively referred to as non-strongly focused ultrasonic beams.

In addition to the above-described focused ultrasonic beam, various types of ultrasonic beams such as the above-mentioned diverged ultrasonic beam, plane ultrasonic beam and virtual source ultrasonic beam, etc., may be collectively referred to as unfocused ultrasonic beam.

Figure 2:
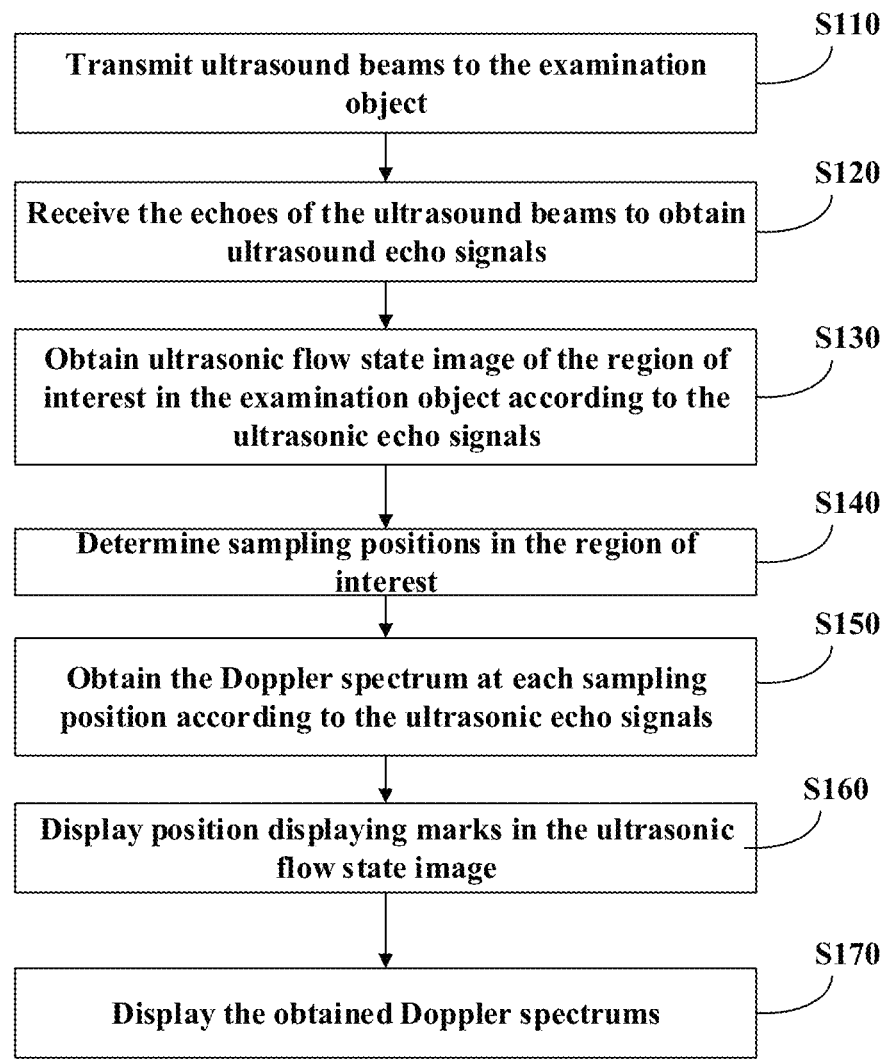
FIG. 2 is a flow chart of one embodiment of the ultrasonic processing method of the present disclosure.
Figure 3:
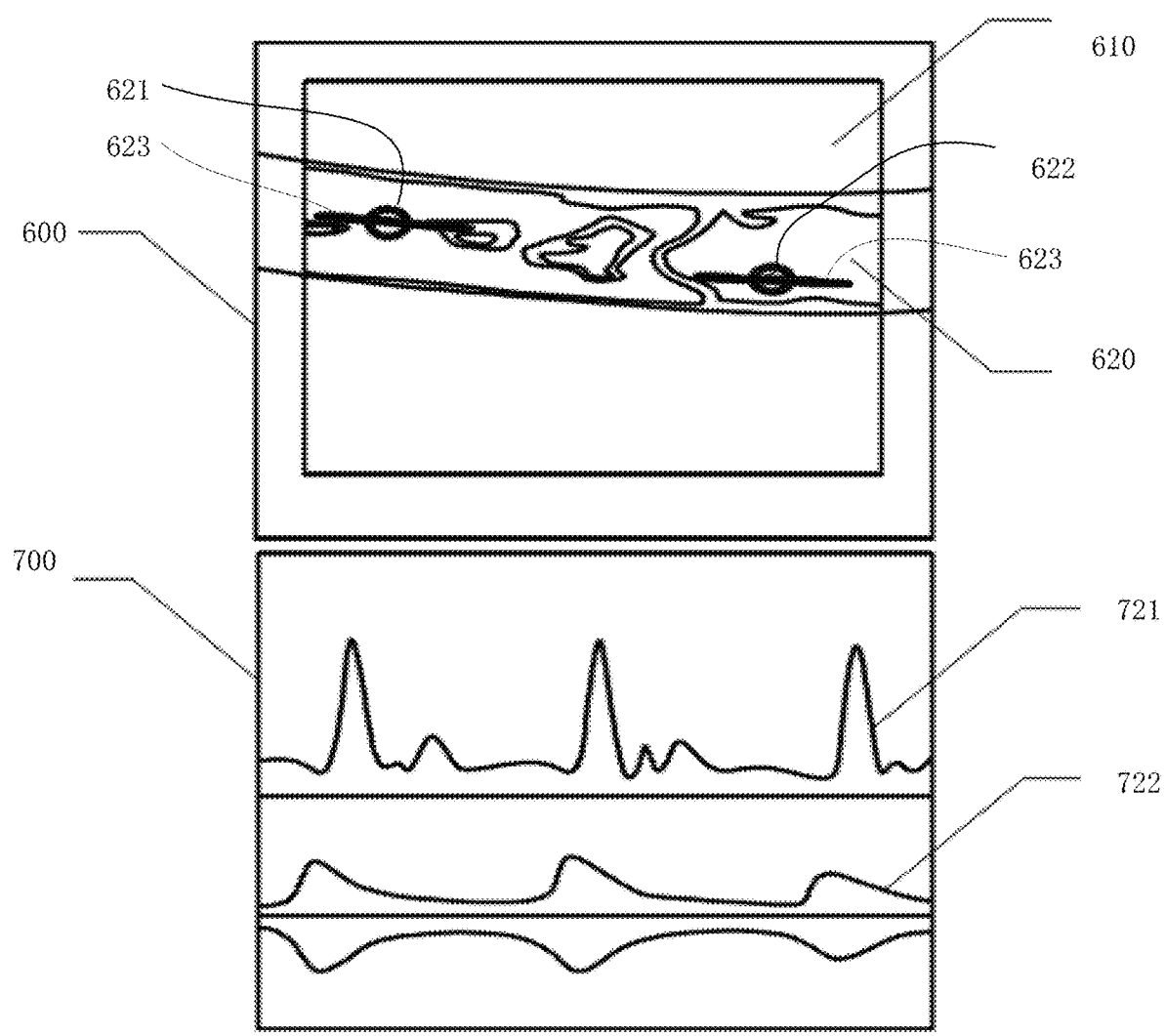
FIG. 3 schematically shows an ultrasonic image obtained by the ultrasonic processing method shown in FIG. 2.

FIG. 2 is a flow chart of one embodiment of an ultrasonic flow spectral Doppler imaging method and FIG. 3 is a schematic diagram showing the results of the embodiment. Referring to FIG. 2 and FIG. 3, in the embodiment, the display 65 may include a first display area 600 and a second display area 700. The first display area 600 may be used for displaying ultrasonic images, and the second display area 700 may be used for displaying Doppler spectrums. The first display area 600 and the second display area 700 may be set in upper and lower manner or left and right manner.

In step S110, the transmitting circuit may excite the probe to transmit an ultrasonic beam to the examination object. In step S120, the receiving circuit and the beam-former may receive the echoes of the ultrasonic beam transmitted in step S110 to obtain ultrasonic echo signals.

The ultrasonic beams transmitted to the examination object may be in multiple groups. During the transmitting process, the probe may be excited in time series to transmit multiple groups of ultrasonic beams, and receive the echoes of the multiple groups of ultrasonic beams returned from the examination objects to obtain multiple groups of ultrasonic echo signals to form a sequence of ultrasonic images having a time series, thereby obtaining source data for dynamic image display. The source data may be used for generating dynamic ultrasonic flow state images. The dynamic ultrasonic flow state images may be displayed in the first display area 600 of the display.

The transmitting circuit may excite the probe to transmit a group of ultrasonic beams to the examination object, and the receiving circuit and the beam-former may receive echoes of the group of ultrasonic beams to obtain a group of ultrasonic echo signals. The transmitting of each group of ultrasonic beams may include the step of transmitting an ultrasonic beam to the examination object at least once. Each group of ultrasonic beams may be transmitted in one transmission direction to obtain ultrasonic beams in a single transmission angle. Alternatively, the groups of ultrasonic beams may be transmitted in a plurality of different transmission directions to obtain a plurality of ultrasonic beams in different transmission angles. In one embodiment, each group of ultrasonic beams transmitted to the examination object may include a plurality of ultrasonic beams in different transmission angles, and the receiving circuit and the beam-former may receive echoes of the plurality of ultrasonic beams in different transmission angles to obtain multiple ultrasonic echo signals contained in one group of ultrasonic echo signals. Based on the multiple ultrasonic echo signals, the ultrasonic echo signals obtained at the same spatial position may be spatially combined and then sent to the signal processor. The echo signals of a plurality of ultrasonic beams in different transmission angles are used to synthesize one frame of ultrasonic image, such that the obtained echo signals can have a higher signal-to-noise ratio while the imaging frame rate can be ensured, thereby obtaining ultrasonic image data with better quality. In addition, velocity vectors of a flow such as a blood flow can be calculated based on echoes of ultrasonic beams in a plurality of different transmission angles, thereby increasing the calculation speed of the velocity vector and obtaining a more real-time flow velocity monitoring result.

Figure 10:
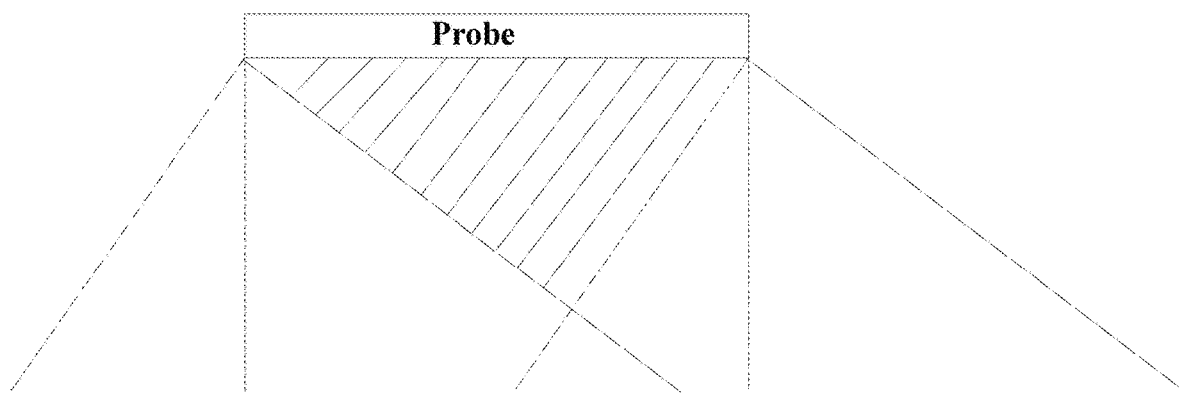
FIG. 10 is a schematic illustration of a multi-angle transmitted ultrasonic beam in one embodiment.

Each element of the probe may be driven by a coded sequence of a base sequence used as driving pulses, and each pulse in the sequence is commonly referred to as a chip. The base sequence may be phase coded using an N-bit transmit code to produce N-chip coded sequences that may be stored in a transmit sequence memory (not shown). Each coded sequence read from the transmit sequence memory may control the activation of the transmit circuit during the respective transmitting. For example, in one embodiment of the present disclosure, each group of ultrasonic beams transmitted by the probe excited by the transmitting circuit to the examination object may include multiple times of transmitting to the examination object, and each transmitting may correspondingly obtain ultrasonic echo signals one time, which may be used to obtain better ultrasonic image by spatial combination. The ultrasonic beams that are transmitted to the examination object multiple times may have the same or different transmission angles. When each group of ultrasonic beams transmitted to the examination object includes a plurality of ultrasonic beams in different transmission angles or includes multiple sub-groups of ultrasonic beams in different transmission angles, the ultrasonic beams may be alternately transmitted to the examination object according to the different transmission angles. Alternately, a plurality of unfocused ultrasonic beams may be alternately transmitted to the examination object in accordance with the difference in the transmission angle. As shown in FIG. 10, the probe may transmit plane ultrasonic beams to the examination object at multiple angles. In the figure, different lines are used to distinguish different transmission angles. When performing spatial combination of the ultrasonic echo signals, the ultrasonic echo signals at the oblique line regions in FIG. 10 will be superimposed.

The ultrasonic beams in step S110 may include one or two or more kinds of non-strongly focused ultrasonic beam, and the non-strongly focused ultrasonic beams may be selected from a plane ultrasonic beam, a diverged ultrasonic beam, and a weakly focused ultrasonic beam, etc. For example, in one embodiment, non-strongly focused ultrasonic beams (here including one or two or more kinds of non-strongly focused ultrasonic beam) may be transmitted to the examination object, and echoes of the non-strongly focused ultrasonic beams may be received to obtain non-strongly focused ultrasonic echo signals which may be used to generate the ultrasonic flow state image of the region of interest in the examination object and/or the Doppler spectrum corresponding to the sampling position.

In addition, the ultrasonic beams in step S110 may be a combination of non-strongly focused ultrasonic beams and focused ultrasonic beams. For example, in one embodiment, non-strongly focused ultrasonic beams (which may include one or two or more kinds of non-strongly focused ultrasonic beams) may be transmitted to the examination object, and the echoes of the non-strongly focused ultrasonic beams may be received to obtain non-strongly focused ultrasonic echo signals which may be used to obtain a Doppler spectrum corresponding to each sampling position. Focused ultrasonic beams may be transmitted to the examination object, and the echoes of the focused ultrasonic beams may be received to obtain focused ultrasonic echo signals which may be used to obtain background ultrasonic images. The background ultrasonic image may be 2D or 3D images in B mode, C mode or other mode. It is also possible to obtain flow information in the region of interest in the examination object according to the focused ultrasonic echo signals. The flow information may be superimposed on the background ultrasonic image to form the ultrasonic flow state image. The flow information herein may include the trend of the flow signal for mapping the flow state of the flow, the magnitude and direction of the flow velocity, etc. For example, the magnitude and direction of the flow velocity may be represented by flow velocity vectors, and the trend of the flow signal may be represented by the trend of the variance of the signals, the time-varying amplitude trend of the signal envelope or the signal energy, etc. The use of focused ultrasonic beams can make the tissue area in the background ultrasonic image clearer and the image quality better.

In one embodiment, non-strongly focused ultrasonic beams (which may include one or two or more kinds of non-strongly focused ultrasonic beams) may be transmitted to the examination object, and echoes of the non-strongly focused ultrasonic beams may be received to obtain non-strongly focused ultrasonic echo signals in a predetermined time period. The non-strongly focused ultrasonic echo signals may be used to obtain corresponding Doppler spectrum at each sampling position in the same predetermined time period, thereby achieving synchronously displaying multiple Doppler spectrums corresponding to multiple sampling positions. Further, in order to improve the display effect and the display speed of the flow state, focused ultrasonic beams may be transmitted to the examination object, and the echoes of the focused ultrasonic beams may be received to obtain focused ultrasonic echo signals which may be used to obtain a background ultrasonic image. The background ultrasonic image herein may be two-dimensional or three-dimensional images in B mode, C mode or other mode. It is also possible to obtain flow information in the region of interest in the examination object according to the echo signals of the transmitted non-strongly focused ultrasonic beams and superimpose the flow information on the background ultrasonic image to form an ultrasonic flow state image.

When a combination of two or more types of ultrasonic beams is used, the multiple types of ultrasonic beams may be alternately transmitted to the examination object. Each type of ultrasonic beam may be successively transmitted at least once. In one embodiment, during the transmission of each type of ultrasonic beam, this type of ultrasonic beams may be transmitted to the examination object in a single transmission angle or in multiple different transmission angles. "Multiple" herein may means that it is greater than or equal to two.

The diverged ultrasonic beam may be regarded as an unfocused wave whose virtual focus is behind the probe. Therefore, the position of the virtual focus can be adjusted by adjusting the delay between the times when the elements participating in the transmission of the ultrasonic waves are excited by the transmission pulses, thereby changing the transmission direction of the unfocused beam. In one embodiment, each group of ultrasonic beams transmitted by the transmitting circuit exciting the probe to the examination object may further include multiple unfocused ultrasonic beams with virtual focuses at different positions. According to the position of the virtual focus, the diverged ultrasonic beams may be alternately transmitted to the examination object. Alternatively, according to the position of the virtual focus, the diverged ultrasonic beam may be alternately transmitted to the examination object for multiple times.

Whether it is a plane ultrasonic beam, a focused ultrasonic beam or a diverged ultrasonic beam, the steer angle or the position of the virtual focus of the resultant beam between the direction of the resultant beam and the normal direction of the plane on which the elements are arranged can be adjusted by adjusting the delay between the time when the elements participating in the transmission of the ultrasonic wave are excited by the transmission pulses, thereby changing the transmission angle of the ultrasonic beam and obtaining different transmission directions of the ultrasonic beams. The resultant beam here may be the plane ultrasonic beam, the focused ultrasonic beam, the virtual source ultrasonic beam or the diverged ultrasonic beam above, and so on.

In the system shown in FIG. 1, the probe may be excited N times by the supplied pulse sequence, thereby transmitting N non-strongly focused ultrasonic beams to the examination object. The transmitting circuit may drive the probe such that the generated ultrasonic energy is guided or manipulated to cover the entire scanning surface in one ultrasonic beam, which may have higher frame rate and faster data acquisition speed than conventional method using focused ultrasonic beams in gray-scale blood flow imaging system. By appropriately adjusting the time delay of the transmission, the non-strongly focused ultrasonic beam can be transmitted to the desired steer angle or virtual focus position, thereby improving the calculation speed of the Doppler spectrum. Furthermore, the Doppler spectrums corresponding to multiple sampling positions may be obtained at the same time, and the obtained Doppler spectrums can be synchronously displayed.

Based on the structure shown in FIG. 1, the present disclosure may employ non-strongly focused ultrasonic beams, by which multiple scan lines or one whole frame of image can be obtained in one transmission. The frame rate can be increased by 10-100 times. Wall filtering may be performed on the acquired signals to obtain blood flow signals, which will be more conducive to blood flow signal acquisition, thereby greatly improving the time resolution of the ultrasonic images and solving the problem of distortion of traditional gray-scale blood flow imaging in displaying high-speed blood flow. For example, when plane ultrasonic beams are used, the image frames are continuously obtained, and the transient state may not be necessary to be considered in filtering, and multiple images can be used for wall filtering to improve the signal-to-noise ratio without loss in frame rate.

In step S120, the receiving circuit and the beam-former may receive the echoes of the multiple groups of ultrasonic beams transmitted in step S110 to obtain multiple groups of ultrasonic echo signals. The ultrasonic echo signals generated by each of the ultrasonic energy bursts (i.e., ultrasonic beams) are reflected from objects that are located in a series of ranges along each of the transmitted beams. The ultrasonic echo signals are detected by the probe, respectively, and the samples of the amplitude of the ultrasonic echo signal at a certain time point may represent the amount of reflection that occurs at a certain range. Due to the difference in propagation paths between the reflection point and each element in the probe, the ultrasonic echo signals will not be detected simultaneously and their amplitudes are not equal. The receiving circuit may receive the electrical signals generated by the probe to obtain corresponding ultrasonic echo signals, and send the ultrasonic echo signals to the beam-former. The beam-former may perform focus-delay, weighting and channel summation, etc. on the ultrasonic echo signals. The beam-former may track the direction of the transmitted ultrasonic beam and sample the ultrasonic echo signals along a series of ranges of each ultrasonic beam. The beam-former may assign an appropriate time delay and receiving apodization weight to each of the ultrasonic echo signals, and sum these signals to obtain a resultant ultrasonic echo signal, which may accurately represent the sum of the corresponding signals of multiple receiving channels within a certain range of one unfocused ultrasonic beam. The beamforming can be achieved by setting a receiving-beam-summer. For the ultrasonic beams transmitted with different transmission angles in a same period, the echo signals may be obtained by the receiving circuit. The receiving channel corresponding to each element in the receiving circuit may include an analog-to-digital converter (not shown). The memory of the receiving beam-former may assign an appropriate receiving focus time delay to each of received echo signals and sums the echo signals to obtain a resultant echo signal that may accurately represent the total ultrasonic energy reflected from the scan positions. For each scan position, the time-delayed received signals may be summed at the receiving-beam-summer.

In one embodiment, when each group of ultrasonic beams transmitted to the examination object by the transmitting circuit exciting the probe includes multiple ultrasonic beams with different transmission angles, the echoes of the ultrasonic beams corresponding to the multiple ultrasonic beams with different transmitting angles may be received to obtain multiple times of ultrasonic echo signals. A spatial compounding may be performed on the ultrasonic echo signals obtained from the same spatial position according to the multiple times of ultrasonic echo signals after the beamforming. In the case that the transmitted ultrasonic beam is a plane ultrasonic beam, the received echo signals can be referred to as "plane ultrasonic echo signal", and so on. The name of the corresponding type of the ultrasonic beam may be added before the received "ultrasonic echo signals", such as "plane", "non-strongly focused", "transmission", and the like.

In step S130, the image processor may obtain an ultrasonic flow state image of the region of interest in the examination object based on the ultrasonic echo signals. In the ultrasonic flow state image, a visual effect of dynamic cloud-like flowing clusters in the flow region can be obtained, and/or flowing trajectories can be exhibited in the flow region.

The signal processor may perform signal detection and enhancement processing on the ultrasonic echo signals to obtain flow data including flow information. The image processor may perform data conversion on the flow data after relevant signal processing (including edge enhancement and logarithmic compression, etc.) or the wall-filtered flow data to obtain ultrasonic image sequence to be displayed in the display. The ultrasonic image sequence may be played to obtain a dynamic image. The ultrasonic flow state image may include an ultrasonic image sequence over a time period in order to present a visual dynamic effect in the region of the flow.

The ultrasonic flow state image may be obtained by the following method.

Obtaining a background ultrasonic image within a predetermined time period according to the ultrasonic echo signals, which may also be referred to as an ultrasonic image sequence;

Obtaining the flow information of the region of interest in the examination object within a predetermined time period according to the ultrasonic echo signals. The flow information herein may include information such as a trend of the flow signal representing the flow state, a magnitude and direction of the flow velocity, etc. For example, the magnitude and direction of the flow velocity may be represented by flow velocity vector information, and the trend of the flow signal may be represented by a trend of variance of the signals, a trend of the time-varying amplitude of the signal envelope, or a signal energy, etc.

Superimposing the flow information on the background ultrasonic image based on chronological order to form the ultrasonic flow state image. The ultrasonic echo signals used to obtain the background ultrasonic image and the flow information may be derived from the same type of ultrasonic beams or different ultrasonic beams. For details, please refer to the related descriptions of the foregoing steps S110 and S120. In one embodiment, the background ultrasonic image may be obtained based on the focused ultrasonic echo signals, and the flow information of the region of interest in the examination object may be obtained based on the non-strongly focused ultrasonic echo signals.

In addition, the flow information may be superimposed on the background ultrasonic image by at least one of the following two methods.

Figure 5A:
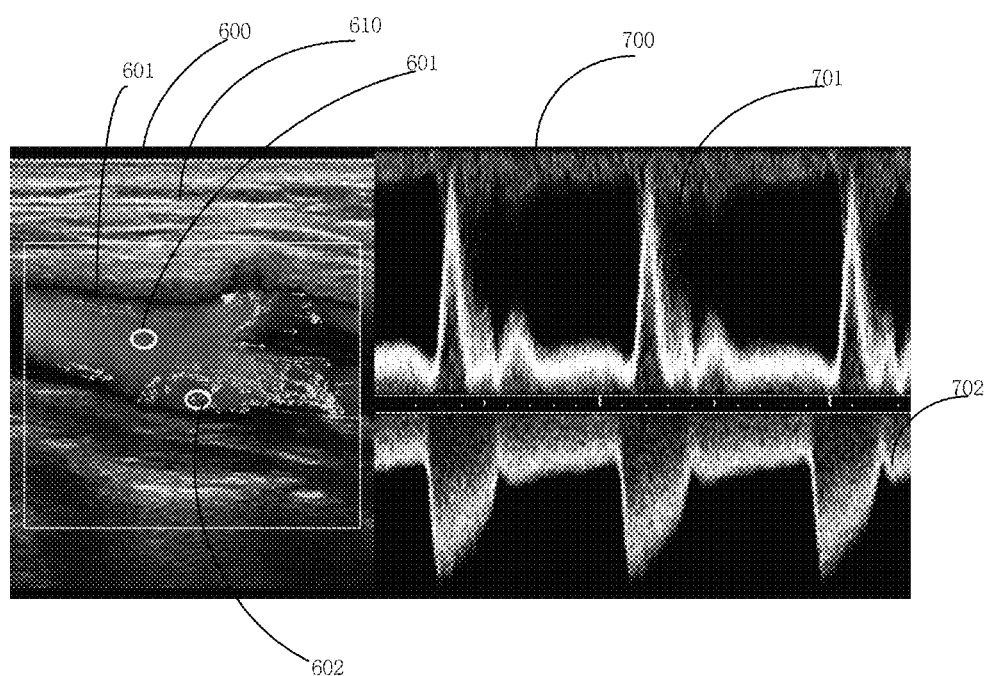
FIG. 5A schematically shows an ultrasonic image based on two sampling positions in one embodiment.
Figure 5B:
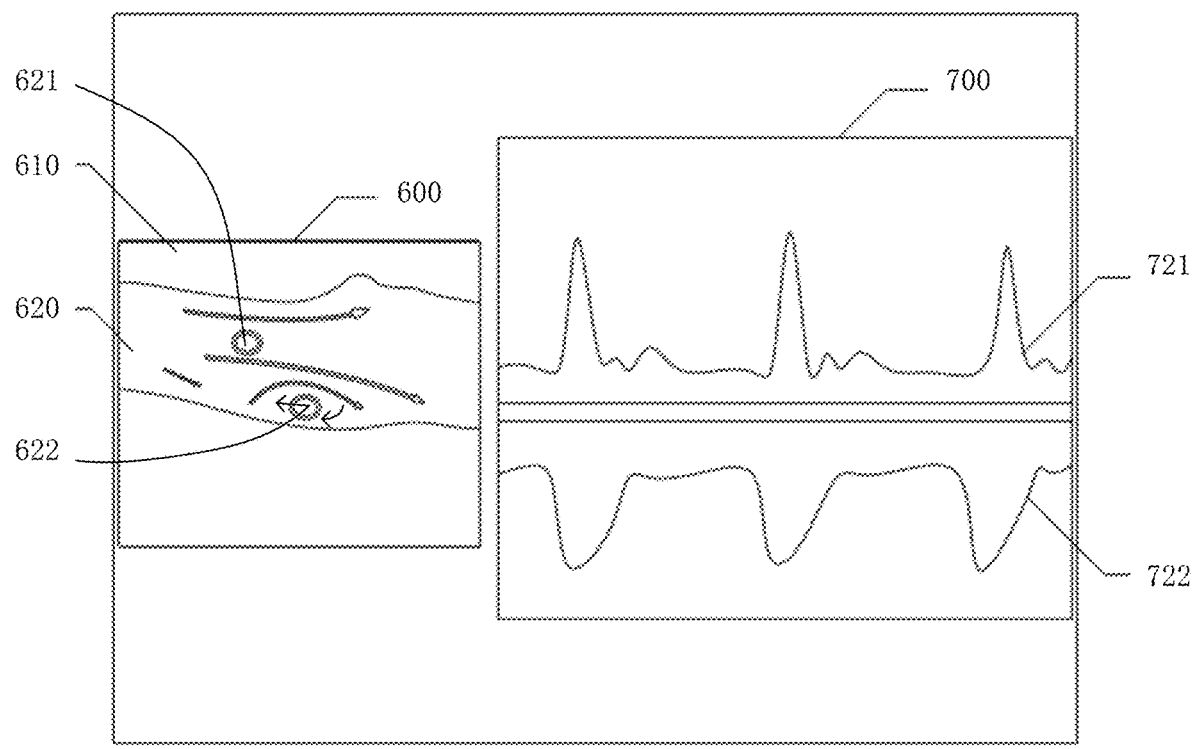
FIG. 5B schematically shows an ultrasonic image based on two sampling positions in another embodiment.

1. Mapping the flow velocity vector information by displaying flow velocity vector identifiers on the background ultrasonic image. The change of the flow velocity vector identifiers may be used to present the change of the flow velocity vector information, thereby obtaining the ultrasonic flow state image and achieving presenting the flowing trajectories of the flow in the flow region in the region of interest, as shown in FIG. 5A and FIG. 5B.

The attributes of the flow velocity vector identifier may be related to the flow velocity vector information. The flow velocity vector identifier may be distinguished from the background image by configuring one or more of the attribute parameters of the color, transparency, contrast and shape of the flow velocity vector identifier. For example, the color of the identifier may be red, yellow, blue, etc., and the shape of the identifier may be arrows of various shapes, dots, triangle points, squares, and the like. For a flow velocity vector identifier with a shape of arrow, the line type may also be an attribute of the shape of the identifier. Moreover, in one embodiment of the present disclosure, the transparency of the identifier may be adjustable. Alternatively, the transparency of the identifier may be gradual. For example, an identifier whose transparency varies between 50-100% may be provided on the background image. In one embodiment of the present disclosure, the magnitude of the velocity in the flow velocity vector information may be represented by one or more attribute parameters of the size, color, transparency and contrast of the flow velocity vector identifier, and the direction information of the flow velocity vector information may be represented by the pointing direction of the flow velocity vector identifier. For example, the flow velocity vector information may be identified by an arrow, where the direction information may be represented by the pointing direction of the arrow and the magnitude of the velocity of the flow may be represented by the length of the arrow.

The position of the flow velocity vector identifier in the background ultrasonic image may correspond to the position of the target point at which the flow velocity vector information is calculated. Specifically, the position of the target point in the background ultrasonic image may be first determined, and then the flow velocity vector identifier may be marked at the position to represent the flow velocity vector information corresponding to the target point (the flow velocity vector information may include the magnitude and direction of the velocity). For example, taking blood flow ultrasonic imaging as an example, in one embodiment, the ultrasonic flow state image may be an ultrasonic blood flow projection image in which the flow velocity vector identifier may be displayed to map the blood flow velocity vector information. Specifically, the blood flow velocity vector information corresponding to one or more target points may be calculated according to the ultrasonic echo signals, and the blood flow velocity vector identifiers may be displayed at positions corresponding to the one or more target points on the background image to represent the blood flow velocity vector information. When the ultrasonic blood flow projection images are continuously played, the change of the flow velocity vector identifier at the corresponding target point display positions may be shown, which may present the flow motion trajectory of the flow. The multiple target points in this embodiment may be specified position points input by the user. Alternatively, the system may automatically disperse a plurality of target points in the flow area in the ultrasonic image. The blood flow velocity vector information herein may include at least the blood flow velocity vector at the target point (i.e., the velocity magnitude and the velocity direction of the blood flow). The blood flow velocity vector information may further include the position information of the target point in the ultrasonic image. Of course, the blood flow velocity vector information may also include any other information about the velocity of the target point that can be obtained according to the magnitude and direction of the velocity of the blood flow, such as acceleration information, etc. In one embodiment, the blood flow velocity vector may be identified by an arrow, where the pointing direction of the arrow represents the direction of velocity of the blood flow, and the length of the arrow represents the magnitude of the velocity of the blood flow. When the ultrasonic blood flow projection images are continuously played, it can be observed that, at the corresponding target point display position, the length and direction of the arrows change with time, which represents the motion trajectories of the flow. This display mode may be referred to as a first display mode of the ultrasonic blood flow projection image.

The position of the flow velocity vector identifier in the background ultrasonic image may be related to the position of the target point at which the flow velocity vector information is calculated. Specifically, the blood flow velocity vectors correspondingly obtained when the target point is continuously moved to the corresponding positions may be marked on the background ultrasonic image to form the flow velocity vector identifier which flows with time to depict the flow trajectory of the flow. For example, taking the blood flow ultrasonic imaging as an example, according to the ultrasonic echo signals, the blood flow velocity vectors sequentially obtained by continuously moving the target point to corresponding positions in the ultrasonic image may be calculated, thereby obtaining the blood flow velocity vector information at the target points. In the present embodiment, the blood flow velocity vectors of the target point moved from one position to another position of the ultrasonic image in a time interval may be repeatedly calculated to obtain the blood flow velocity vectors of the target point at the corresponding positions to which the target point is moved from the initial position. That is to say, in the present embodiment, the calculation position for determining the blood flow velocity vector in the ultrasonic image may be obtained by calculation, and the initial position may be a specified position input by the user. Alternatively, the system may automatically disperse multiple target points in the ultrasonic image.

In the display mode of the present embodiment, the displacement of the target point at a time interval may be calculated, and the corresponding position of the target point in the ultrasonic image may be determined according to the displacement. The target point is moved from an initially selected target point position according to the time interval. The time interval may be determined by the transmission frequency of the system or the display frame rate. Alternatively, the time interval may be input by the user. The positions to which the target point is moved may be calculated according to the time interval input by the user, and the blood flow velocity vector information at the positions may be obtained for comparison display. Initially, N initial target points may be marked in the image according to the manners shown in FIG. 5A, FIG. 5B and FIG. 6. At each initial target point, there may be an arrow which represents the magnitude and direction of the flow velocity at this point, as shown in FIG. 5A. Thereafter, the blood flow velocity vector information at the positions to which the target point is successively moved to may be calculated. The flow velocity vector identifiers may be marked at the corresponding positions to correspondingly represent the calculated blood flow velocity vector information. As time changes, in the newly generated image, the position of the arrow of each point will change position. This way, the movement of the arrow can form a flow similar to blood flow such that the user can observe the approximate true blood flow effect. This display mode is referred to herein as the second display mode of the ultrasonic blood flow projection image. Similarly, although only two-dimensional display effect diagrams are given in the drawing, it can also be applied to three-dimensional image, that is, the ultrasonic image at the moments may be three-dimensional image data obtained by scanning body, and the position of the target point may be the spatial three-dimensional coordinate position in the three-dimensional image data, which will not be described again here.

In the calculation process above, the flow velocity vector information may be calculated according to the ultrasonic echo signals. Hereinafter, blood flow ultrasonic imaging is taken as an example, and several methods are provided for reference to obtain flow velocity vector information. However, the present disclosure will not be limited to these methods.

First, the ultrasonic beams may be transmitted to the examination object in one ultrasonic wave propagation direction, and echoes of the ultrasonic beams may be received to obtain one group of ultrasonic echo signals. At least two frames of image data may be obtained according to the one group of ultrasonic echo signals. A tracking area may be selected in a first frame of image data, and a tracking result area corresponding to the tracking area may be searched in the second frame of image data. According to the positions of the tracking area and the tracking result area and time interval between the first frame of image data and the second frame of image data, the blood flow velocity vector information of the target point may be obtained.

Second, the ultrasonic beams may be transmitted to the examination object in two or more ultrasonic wave propagation directions, and echoes of the ultrasonic beams may be received to obtain one group of ultrasonic echo signals including multiple ultrasonic echo signals which includes echoes originating from the ultrasonic beams transmitted in different ultrasonic wave propagation directions. According to the one group of ultrasonic echo signals, the blood flow velocity information in different ultrasonic wave propagation directions may be calculated, where the direction of the blood flow velocity information is the propagation direction of the ultrasonic beam. This way, the blood flow velocity vector information in different ultrasonic propagation directions may be obtained. Thereafter, a resultant blood flow velocity vector having one direction may be obtained by spatial synthesis of the velocity vectors. The resultant blood flow velocity vector may be used as the blood flow velocity vector information of the target point. The blood flow velocity calculated by this way may be more close to the real situation. The method for calculating the blood flow velocity information in a single ultrasonic propagation direction may be a Doppler velocity measurement method.

Third, according to the ultrasonic echo signals, the Doppler velocity measurement method may be used to calculate the blood flow velocity information corresponding to the target point of which the velocity direction is the propagation direction of the ultrasonic beams, thereby obtaining the blood flow velocity vector information corresponding to the target point.

2. Mapping the trend of the collected flow signals by image grayscale and/or image color information on the background ultrasonic image to obtain the ultrasonic flow state image to present dynamically moving cloud-like flowing clusters, thereby visually presenting the flowing state of the flow, as shown in FIG. 3.

The quadrature demodulated signals after the relevant signal processing include I and Q signals. The I and Q signals may be separately subjected to wall filtering processing. In the ultrasonic imaging system shown in FIG. 1, the following methods may be used to obtain corresponding image data based on the I and Q demodulated data before and after the filtering.

The image processor may calculate the variance of the I and Q demodulated data in the flow data, distinguish the non-flow image region (for example, tissue region) and the flow image region according to the variance, and map the trend of the variance with image grayscale and/or image color information to obtain a B-mode ultrasonic image sequence superimposed with image grayscale and/or image color information, or obtain a B-mode ultrasonic image sequence in which the image grayscale and/or image color information is superimposed according to different region. A large variance may indicate a flow, while a small variance may indicate a non-flow that is stationary.

The variance may be calculated as follows:

The variance Var may be expressed as the following formula (1):

$$V_{ar} = \frac{(I_{i+1}I_i + Q_{i+1}Q_i)^2 + (Q_{i+1}I_i - I_{i+1}Q_i)^2}{I_i^2 + Q_i^2} \quad \text{Formula (1)}$$

Where i is a natural number, i=1, . . . , N, which indicate the sampling time. Ii represents the I-th demodulated data at the i-th time, and Qi represents the Q-th demodulated data at the i-th time.

The variance Var may also be expressed as the following formula (2).

$$\text{Var} = \frac{\left(\sum_{i=0}^{N} I_{i+k}I_i + Q_{i+k}Q_i\right)^2 + \left(\sum_{i=0}^{N} Q_{i+k}I_i - I_{i+1}Q_i\right)^2}{R(0)} \quad \text{Formula (2)}$$

Where k is an integer, k=0, 1, 2, 3, . . . . R(0) represents the flow signal energy obtained by the Leg-zero method, and may be specifically expressed by the following formula (3).

$$R(0) = \sum_{i=0}^{N} \frac{I_i^2 + Q_i^2 + I_{i+k}^2 + Q_{i+k}^2}{2(N+1)} \quad \text{Formula (3)}$$

The variance at the corresponding positions may be calculated according to the formula (1) and formula (2) above, and different image grayscale and/or image color information may be mapped according to the trend of the variance. The image grayscale and/or image color information may be superimposed on the B mode ultrasonic images obtained by the image processor to achieve display effect. For example, overall image grayscale information mapping may be performed on the variances of the positions in the entire image. When the B-mode ultrasonic image sequence obtained by superimposing the image grayscale on the B-mode ultrasonic images is played to present the dynamic visual effects, the grayscale effect may be presented in the full-frame image and dynamic blocky or cloud-like flowing clusters may be presented in the flow region. For example, the overall image color information mapping may be performed on the variances at the positions in the entire image. When the B-mode ultrasonic image sequence obtained by superimposing the image color information on the B-mode ultrasonic images is played to present the dynamic visual effects, a color contrast effect may be presented in the full image and dynamic colored cloud-like flowing clusters may be presented in the flow region. It is also possible to distinguish the non-flow image positions and the flow image positions according to a variance threshold, and map the image color information according to the trend of the variance and superimpose the image color information in the image position area of the flow. Different image colors may be obtained by changing one of hue, transparency and saturation. Mapping the image colors at different positions according to the trend of the variances may obtain corresponding image color information.

The flow data containing the flow information after the wall filtering process may be converted to obtain the B mode ultrasonic image sequence by one the following methods.

First, the variance may be calculated according to the I and Q demodulated data in the wall-filtered flow data, and the trend of the variance may be mapped with image grayscale and/or image color information to obtain the B-mode ultrasonic image sequence. The method for calculating the variance may be those of formula (1) to formula (3) above.

Second, the I and Q demodulated data in the wall-filtered flow data may be converted from a polar coordinate system into a Cartesian coordinate system, and the trend of the time-varying amplitude of the signal envelope may be mapped with image grayscale and/or image color information to obtain the B-mode ultrasonic image sequence. For example, representing the blood flow image as Flow_image (x,z), the conversion of the B-mode ultrasonic image sequence may be as following formula (4):

$$\text{Flow\_image}(x,z) = \sqrt{I^2(x,z) + Q^2(x,z)} \qquad \text{Formula (4)}$$

The value of each point on the image may be directly obtained. This first method is similar to the conventional B-picture imaging method.

Third, according to the I and Q demodulated data in the wall-filtered flow data, the signal energy representing the flow may be calculated, and the magnitude of the signal energy may be mapped with image grayscale and/or image color information to obtain the B mode ultrasonic image sequence. For example, the Leg-zero method may be used to obtain the energy of the blood flow signal, and the calculation method can be referred to the above formula (3).

When the image data has only one path of data, the Hilbert transform may be performed on the RF data of the image along the depth to obtain the I and Q data, and then the wall filtering process may be performed. Thereafter, the B mode ultrasonic image sequence may be obtained by one of the above three methods.

The image processor may further configured to calculate the signal energy representing the flow according to the wall-filtered flow data, divide the flow position area and the non-flow position area in the ultrasonic image data based on an energy threshold, and superimpose the wall-filtered flow data on the flow position area and perform the data conversion to obtain the B-mode ultrasonic image sequence. This allows the obtained image data to have clearer and more accurate flow image information.

The signal energy at the corresponding display positions may be calculated according to the formula (3) above, and different image grayscales and/or image color information may be mapped according to the trend of the signal energy. The image grayscales and/or image color information may be superimposed on the B mode ultrasonic images obtained by the image processor, thereby achieving the display effects. For example, overall image grayscale information mapping may be performed on the signal energy of the positions in the entire image. When the B-mode ultrasonic image sequence obtained by superimposing the image grayscale on the B-mode ultrasonic images is played to present the dynamic visual effects, the grayscale effect may be presented in the full-frame image and dynamic blocky or cloud-like flowing clusters may be presented in the flow region. For example, the overall image color information mapping may be performed on the signal energy at the positions in the entire image. When the B-mode ultrasonic image sequence obtained by superimposing the image color information on the B-mode ultrasonic images is played to present the dynamic visual effects, a color contrast effect may be presented in the full image and dynamic colored cloud-like flowing clusters may be presented in the flow region. It is also possible to distinguish the non-flow image positions and the flow image positions according to a signal energy threshold, and map the image color information according to the trend of the signal energy and superimpose the image color information in the image position area of the flow. Different image colors may be obtained by changing one of hue, transparency and saturation. Mapping the image colors at different positions according to the trend of the signal energy may obtain corresponding image color information.

3. The display manners in 1 and 2 above may both be used, that is, in the ultrasonic image, not only the flow velocity vector identifier is displayed to map the flow velocity vector information, but also the image grayscale and/or image color information are used to map the trend of the collected flow signals, thereby obtaining the ultrasonic flow state image which simultaneously presents a dynamic cloud-like flowing cluster in the flow region and the flow trajectory of the flow.

In step S140, the image processor may determine the sampling positions in the region of interest, where the number of the sampling positions may be greater than or equal to two. In step S150, the image processor may respectively obtain the Doppler spectrum corresponding to each sampling position according to the ultrasonic echo signals. The ultrasonic echo signals herein may be any one of non-strongly focused ultrasonic echo signals.

The sampling position may include one pixel or an area containing multiple pixels ("multiple" herein may mean greater than or equal to two). In the case that the sampling position is one pixel, the Doppler spectrum may correspond to the position of the pixel. In the case that the sampling position is an area containing multiple pixels, the Doppler spectrum of such sampling position may be obtained according to the Doppler spectrum of the center point of the area, the mean of the Doppler spectrum of the pixels in the area or the variance of the Doppler spectrum of the pixels in the area, etc.

In one embodiment, the image processor may first calculate the Doppler spectrum corresponding to the sampling positions according to the ultrasonic echo signals, and then generate the Doppler spectrum with a horizontal axis of time and a vertical axis of Doppler spectrum information based on the Doppler spectrum. The Doppler velocity measurement method may be used to calculate the Doppler velocity information corresponding to the sampling position. For example, taking the blood flow Doppler velocity measurement as an example, a segment of signal may be selected from the wall-filtered signals, and the Fourier transform may be performed on the segment of signal to obtain the blood flow spectrum which represents the change of frequency over the time period of this segment of signal. This frequency is the Doppler frequency that represents the velocity of the blood flow. Therefore, it can be regarded as a distribution map of the number of red blood cells with different velocities in the blood flow at this time. Then, the next segment of signal may be selected, and the distribution map of the number of red blood cells with different velocities in the blood flow at this time may be generated again. Thereafter, the distribution map of each time may be displayed vertically in the form of gray scale in the order of time, thereby forming the blood flow Doppler spectrum.

In the embodiment of the present disclosure, in addition to the focused wave, the non-strongly focused ultrasonic beam such as the plane ultrasonic beam, the diverged ultrasonic beam or the weakly focused ultrasonic beam may also be used to obtain the Doppler spectrum information. In this way, the echoes of the entire area may be obtained by one transmission. After the beam-forming, the Doppler spectrum at the same time corresponding to any position on the ultrasonic image may be calculated by the spectrum calculation method above. The spectrum at any one or more of the sampling positions obtained here may be at the same time.

In one embodiment of the present disclosure, taking the blood flow Doppler velocity measurement as an example, the Doppler spectrum corresponding to each sampling position at a same time may be respectively calculated according to the non-strongly focused ultrasonic echo signals in a predetermined time period. The blood flow Doppler spectrum of each sampling position may be arranged according to time, thereby achieving synchronously displaying the blood flow Doppler spectrums of two or more sampling positions on the display.

In step S160, the image processor may generate a position displaying mark, where one position displaying mark corresponds to one sampling position. The position displaying mark may be displayed on the ultrasonic flow state image on the display.

As shown in FIG. 3, in one embodiment of the present disclosure, a new position displaying mark (e.g., 621, 622 in FIG. 3) may be provided. The position displaying mark may include a closed box. The position of the box in the ultrasonic image and the size of the box can be adjusted according to needs of the user. For example, in one embodiment, the position and/or size of the box may be determined based on a box adjustment instruction input by the user. The box adjustment instruction may be originated from the adjustment operation performed by the user to the position and/or size of the box in the region of interest through the human-machine interface.

The operation for adjusting the position of the box in the region of interest may be performed by, but not limited to, one of the following ways.

1. Obtaining an instruction for the user to drag the box through the human-machine interface, determining the current position of the cursor according to the instruction, and changing the position of the box to the current position of the cursor, thereby obtaining the effect that the box moves following the cursor.

2. Obtaining an instruction for the user to select the box, determining the box selected by the user according to the instruction, determining the final position of the cursor after a period of time, and changing the position of the box selected by the user to the final position of the cursor, thereby achieving the position jump of the box.

The operation for adjusting the size of the box in the region of interest may be performed by, but not limited to, one of the following ways.

1. Performing discretization to the edge line of the box to obtain multiple discrete points, determining a movement operation of the user to one or more of the multiple discrete points, changing the positions of the discrete points according to the movement operation, where the changed discrete points form a new edge line of the adjusted box, and determining the size of the box according to the area surrounded by the new edge line.

2. Identifying the user's control instruction to the corner of the box, the center line of the box or the zoom operation, etc., and changing the area surrounded by the edge line of the box to determine the size of the box.

The box herein may be a closed square box, a round box, an elliptical box, a polygonal box, and the like which are formed by edge lines. In FIG. 3, only the position displaying marks 621 and 622 of the round box are given. However, the present disclosure will not be limited thereto. The specific shape of the box herein will not be limited. Any closed box that includes one pixel or a certain area may be used. The "closed" herein may include an approximately closed structure with a slight opening.

The position displaying marker may be used to indicate which sample position in the ultrasonic image the Doppler spectrum displayed corresponds to. During the interaction between the user and the ultrasonic image, the adjustment instruction of the user to the sampling position can be obtained by adjusting the box. For example, in one embodiment, the sampling position may be re-determined based on the box adjustment instruction input by the user, and the Doppler spectrum corresponding to the adjusted sampling position may be calculated. The box adjustment instruction herein may be derived from the operation of the user to the position and/or the size of the box in the region of interest through the human machine interface. Based on the adjustment instruction input by the user, the position corresponding to the Doppler spectrum to be calculated may be determined according to the re-determined sampling position. For example, when the position of the box in the region of interest is changed, the corresponding Doppler spectrum may be obtained according to the updated position. After the area of the box in the region of interest is changed, the Doppler spectrum corresponding to the required sampling position may be generated according to the Doppler spectrum corresponding to any position included in the box area. Alternatively, the Doppler spectrum corresponding to the required sampling position may also be generated according to the average, the variance, the mean square deviation, etc. of the Doppler spectrum corresponding to multiple positions included in the box area. Therefore, when the size of the box area corresponding to the sampling position changes, the corresponding Doppler spectrum may or may not be updated.

In addition to achieving the update of the sampling position by adjusting the position of the position displaying mark, it is also possible to obtain the sampling position directly input by the user in the region of interest and determine the sampling position according to the direct input of the user, and calculate the Doppler spectrum.

The position displaying mark may also include an angle correction line (as indicated by reference numeral 623 in FIG. 3) associated with the box. The angle correction line may include one of a straight line, a line segment and a ray passing through or connecting the box. In one embodiment, the angle between the propagation direction of the ultrasonic beam and the flowing direction of flow may be corrected based on an angle correction instruction input by the user. The angle correction instruction herein may be derived from an adjustment operation of the user to the angle correction line through the human machine interface. For example, as shown in FIG. 3, the initial position of the angle correction line 623 is kept parallel to the blood vessel wall, or is directed to the direction of the blood flow velocity at this position. By adjusting the angle correction line, the angle between the propagation direction of the ultrasonic beam and the flowing direction of the flow may be freely changed such that the user can more intuitively and clearly, more easily judge the direction or manner of correction from the displayed image. The association between the angle correction line and the box may refer to the linkage arrangement of the box and the angle correction line. The specific manner may include the angle correction line passing through the box, the angle correction line being parallel to the central axis of the box and the angle correction line connecting the box, etc.

The process of identifying the sampling position in the region of interest and obtaining the Doppler spectrum corresponding to the sampling position according to the ultrasonic echo signals may include:

obtaining the sampling position according to the determined position and/or size of the box;

obtaining central spectral data corresponding to a center point of the sampling position, or calculating an average of the spectral data at multiple points in the sampling position;

obtaining a Doppler spectrum corresponding to the sampling position according to the central spectrum data or the average of the spectral data at the multiple points.

In step S170, the obtained Doppler spectrum may be displayed on the display. In this embodiment, the obtained Doppler spectrum corresponding to any sampling position may be displayed. Alternatively, the Doppler spectrums corresponding to two or more sampling positions may be simultaneously displayed. In the step of displaying the obtained Doppler spectrum, two or more Doppler spectrums may be displayed based on the same time axis.

Referring to FIG. 3, an ultrasonic flow state image may be displayed in a first display area 600 of the display. The ultrasonic flow state image may be obtained by mapping the trend of the collected flow signal with the image grayscale and/or image color information on the background ultrasonic image 610, which can present dynamically moving cloud-like clusters so as to visually present the flow state. Two position displaying marks 621 and 622 may be displayed in the image, each of which may have a round shape and provided with an angle correction line 623 passing through the round shape. The two position displaying marks 621 and 622 may correspond to two sampling positions, respectively. The Doppler spectrum 721 and the Doppler spectrum 722 corresponding to the two sampling positions may be respectively displayed in the second display area 700. The Doppler spectrum 721 and the Doppler spectrum 722 may be comparatively displayed based on the same time axis.

Referring to FIG. 5A, an ultrasonic flow state image may be displayed in a first display area 600 of the display. The ultrasonic flow state image may be obtained by displaying the flow velocity vector identifier (e.g. the arrow 601 in FIG. 5A) on the background ultrasonic image 610 to map the flow velocity vector information. The change of the flow velocity vector identifier (e.g. the arrow 601 in FIG. 5A) may be used to present the change of the flow velocity vector information, thereby obtaining the ultrasonic flow state image and achieving presenting the flow trajectory of the flow in the flow region in the region of interest. Two position displaying marks 601 and 602 may be displayed in FIG. 5A, each of which may have a round shape. The two position displaying marks 621 and 622 may correspond to two sampling positions, respectively. The Doppler spectrum 701 and the Doppler spectrum 702 corresponding to the two sampling positions may be respectively displayed in the second display area 700. The Doppler spectrum 701 and the Doppler spectrum 702 may be comparatively displayed based on the same time axis.

The position displaying marks may be displayed on the ultrasonic flow state image and associated with the sampling positions. The number of the sampling positions may be equal to the number of position displaying marks. Referring to FIG. 5B, the ultrasonic flow state image may include a background region 610 and a flow region 620. The background region 610 may display the background ultrasonic image described above, while the flow region 620 may display the flow information. The sampling position may usually be set in the flow region. Within the flow region 620, the number, position, size, and shape of the position displaying marks representing the sampling positions may be adjustable. For example, the position displaying mark may be a point, a circle, or other shapes. For example, the position displaying mark may also be enlarged or reduced so as to change the calculation range of the sampling position. In the present embodiment, two position displaying marks 621, 622 are selected in the flow region 620, thereby determining two sampling positions. The Doppler spectrums 721 and 722 obtained at these two sampling positions are respectively displayed in the second display area 700 of the display. In the flow region 620, a long arrow may also be used to present the blood flow trajectory of a certain target point or target region, so as to clearly present the flow motion of different regions of the flow.

Figure 6:
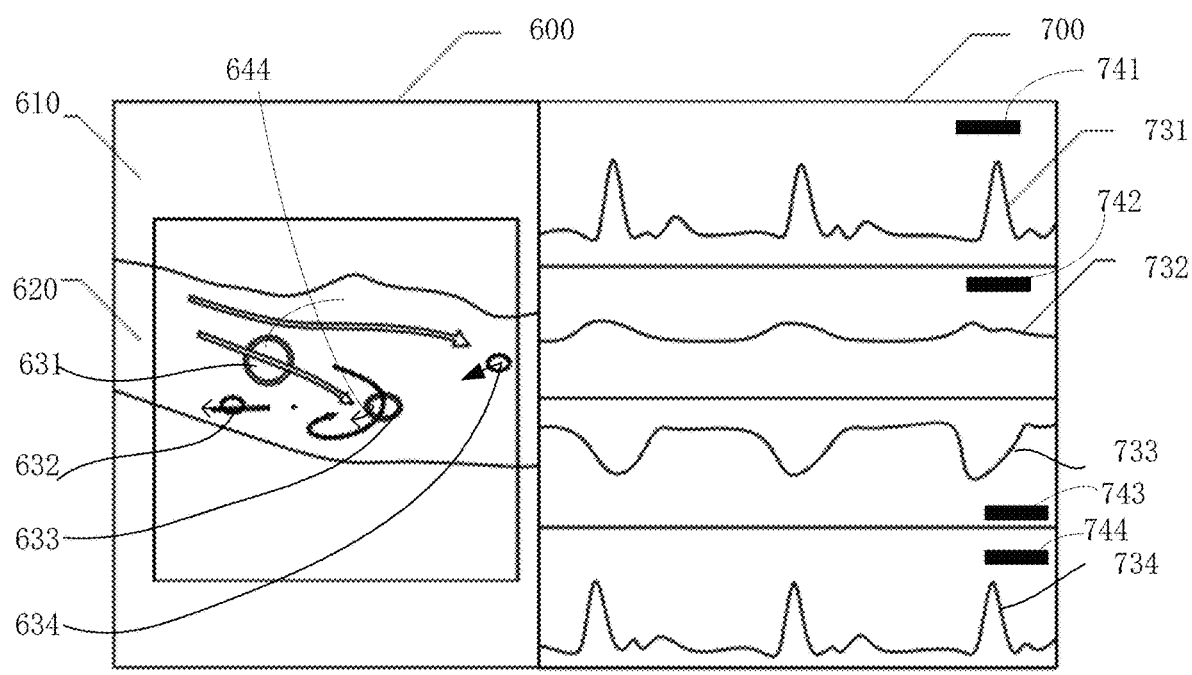
FIG. 6 is an interface of an ultrasonic image based on four sampling positions.

FIG. 6 schematically shows an ultrasonic blood flow projection image based on four position displaying marks in one embodiment of the present disclosure. As shown in FIG. 6, the ultrasonic blood flow projection image may be displayed in the first display area 600, in which the directional line segments represent the velocity vectors of the flow. There may be four sampling positions. The sampling positions may be located at different positions in the flow region, such as the sampling position located in the laminar flow region (position displaying mark 631), the sampling position located in the vortex flow region (position displaying mark 632), the sampling position located in the turbulent flow region (position displaying mark 633) and the sampling position located in the aliasing region (position displaying mark 634). The aliasing region may appear because the flow rate is too fast. The Doppler spectrums 731, 732, 733, and 734 corresponding to the four position displaying marks 631, 632, 633 and 634 are also synchronously displayed on the display. It can be intuitively seen that the flow patterns of blood flow at these four different locations are quite different, and the corresponding spectrums are also quite different. The Doppler spectrums corresponding to different sampling positions may be assigned with different color identifiers, and the position displaying mark and the color identifier of the Doppler spectrum corresponding to the same sampling position may have the same color. The color identifier may be implemented by, but not limited to, the following ways: 1. directly colorizing the Doppler spectrum to form the color identifier, for example, directly rendering the Doppler spectrum (731, 732, 733, 734) with the color of the corresponding position displaying mark (631, 632, 633, 634); 2. providing a separate color identifier for each Doppler spectrum, for example, providing a color strip at position above or below the Doppler spectrum. In FIG. 6, the color strips 741, 742, 743, and 744 are respectively provided to the Doppler spectrums 731, 732, 733, and 734. The color strips and the corresponding position displaying markers (631, 632, 633, 634) have the same color.

Further, on the basis of the embodiment shown in FIG. 2, a comparative display of Doppler spectrum differences may also be provided in order to provide more diagnostic references to the user. For example, in step S130, the image processor may obtain the ultrasonic image of the region of interest in the examination object according to the ultrasonic echo signals. The ultrasonic image may be an ultrasonic flow state image, or other types of ultrasonic image. In step S140, the image processor may determine a first sampling position in the region of interest, and obtain a first Doppler spectrum corresponding to the first sampling position according to the ultrasonic echo signals. The image processor may further determine a second sampling position and obtain a second Doppler spectrum corresponding to the second sampling position according to the ultrasonic echo signals. Thereafter, the image processor may estimate the difference between the first Doppler spectrum and the second Doppler spectrum, and may output the obtained difference using the display and/or audio player.

When evaluating the difference between the first Doppler spectrum and the second Doppler spectrum, the image processor may extract the same attribute parameters in the first Doppler spectrum and the second Doppler spectrum and calculate a difference between the same attribute parameters to obtain the difference between the first Doppler spectrum and the second Doppler spectrum. The way to evaluate the difference between the same attribute parameters may be extracting a certain pulse wave spectrum parameter and calculating the similarity or difference thereof, for example, by subtraction, addition or calculating the ratio, and the like. The same attribute parameters mentioned herein may refer to the same pulse wave (PW) spectrum parameters, which may include, but not limited to, Peak Systole Velocity (PSV), End Diastole Velocity (EDV), Resistance Index (RI), ratio of Peak Systole Velocity to End Diastole Velocity (S/D), Pulsatility Index (PI), Acceleration Time (AT) and heart beats per minute, etc.

Figure 7:
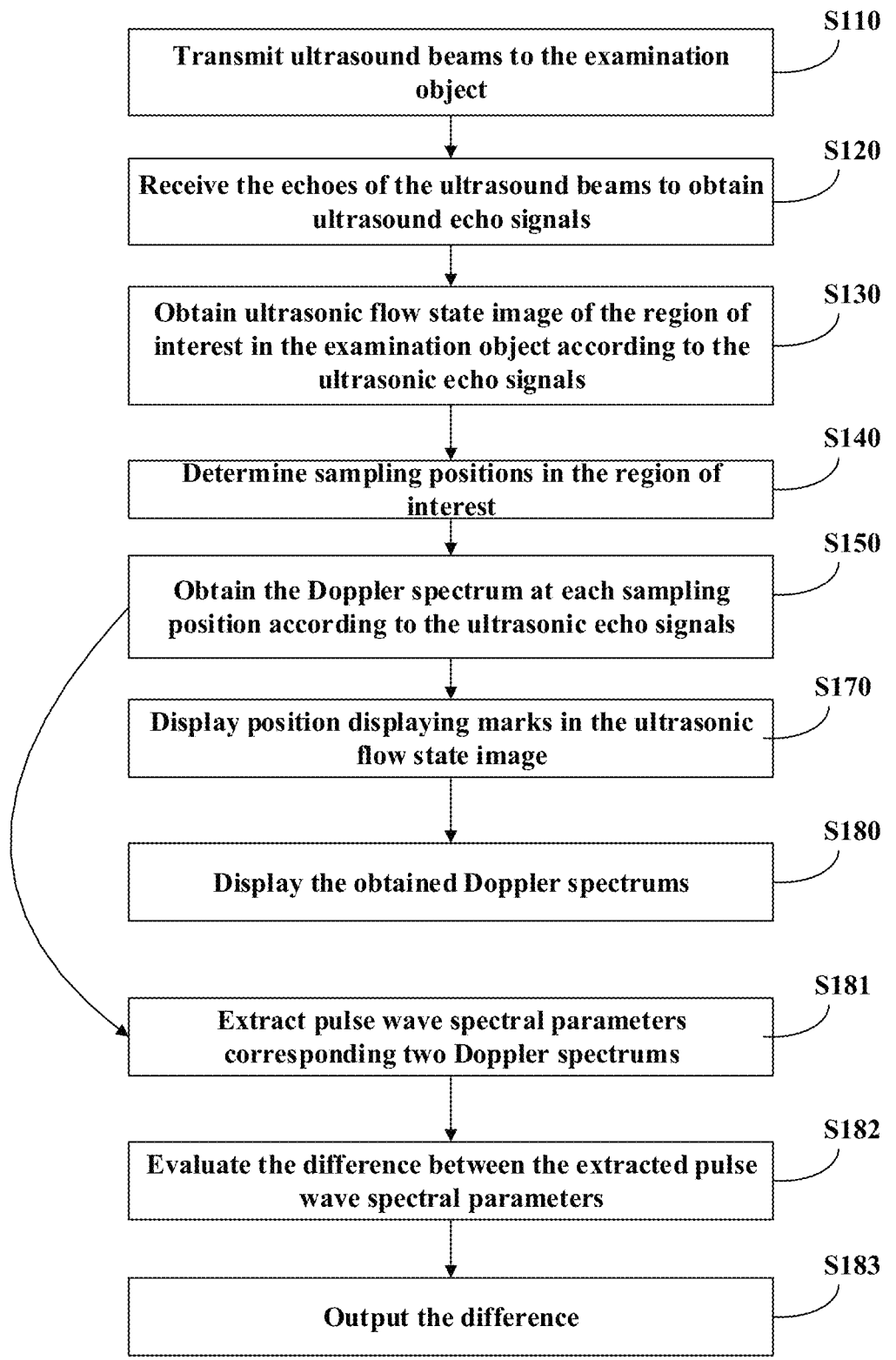
FIG. 7 is a variant embodiment of FIG. 2.

In one embodiment, as shown in FIG. 7, the following steps are further included on the basis of the flow shown in FIG. 2.

In step S181, the image processor may extract the pulse wave spectral parameters corresponding to the two Doppler spectrums.

In step S182, the image processor may evaluate the difference between the extracted pulse wave spectral parameters. The way for evaluating the difference may be extracting a certain pulse wave spectral parameter and calculating the similarity or difference thereof, for example, by subtraction, addition or calculating the ratio, and the like.

In step S183, the difference obtained by the evaluation may be output through the display or the audio player. Various ways for output may be used, such as text, audio prompt, or difference curve, etc.

In one embodiment, a semi-automatic anti-aliasing processing method may also be provided. As shown in FIG. 6, the ultrasonic flow state image displayed in the first display area 600 may be an ultrasonic blood flow projection image, in which the flow velocity vector identifier 644 may be displayed to map the blood flow velocity vector information. The image processor may automatically adjust the attribute of the flow velocity vector identifier in the ultrasonic blood flow projection image according to an aliasing adjustment instruction input by the user. The aliasing adjustment instruction may be derived from the adjustment operation performed by the user to the aliasing position in the Doppler spectrum through the human machine interface. The attribute of the flow velocity vector identifier may include at least one of the shape, the color and the direction of the flow velocity vector identifier. For example, in FIG. 6, the Doppler spectrums 731, 732, 733 and 734 correspond to the position displaying marks 631, 632, 633 and 634, respectively. When the aliasing is found on the Doppler spectrum 733, the spectrum 733 is manually adjusted, and the attribute of the flow velocity vector identifier 644 inside or near the position displaying marker 633 may also be adjusted accordingly. For example, based on the aliasing adjustment instruction input by the user, the velocity direction indication or the velocity magnitude indication of the flow velocity vector identifier 644 may be adjusted, such as changing the length of the arrow and/or changing the pointing direction of the arrow.

Figure 4:
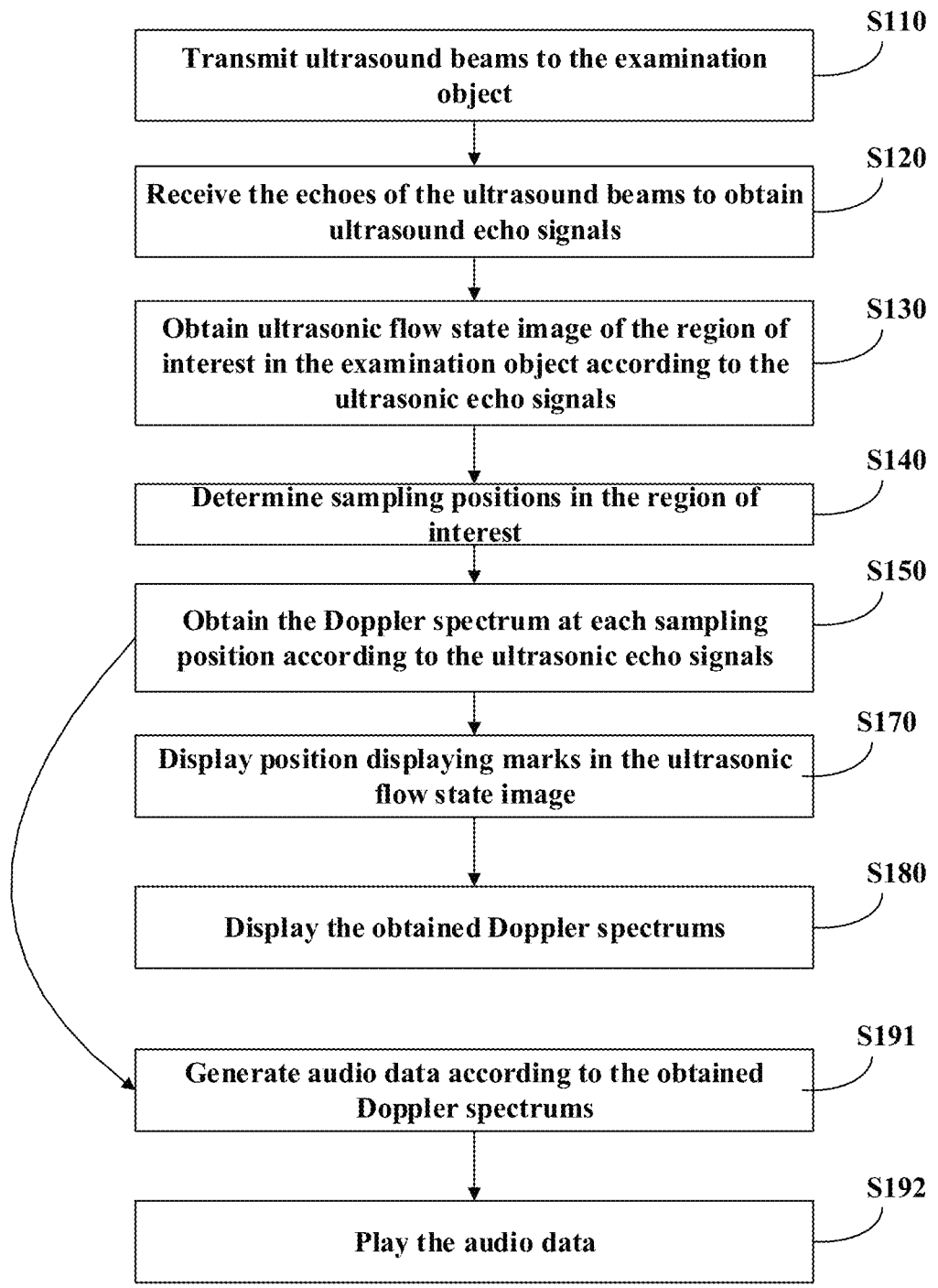
FIG. 4 is a flow chart of another embodiment of the ultrasonic processing method of the present disclosure.

FIG. 4 is a flow chart of another embodiment of the ultrasonic processing method of the present disclosure. In one embodiment, as shown in FIG. 4, based on the flow shown in FIG. 2, the method may further include the step of playing the audio data corresponding to the obtained Doppler spectrum. Specifically, steps S191 and S192 may be added.

In step S191, the audio processor 67 may generate audio data corresponding to each of the sampling positions based on the spectral data of the two or more sampling positions selected by the user.

In step S192, the audio player 69 may play the audio data. The audio player 69 may be a multi-channel player, and each channel may play audio data of one sampling position. In an alternative embodiment, the audio player 69 may use single-channel playback, and mix the audio data of the at least two sampling positions to display. Alternatively, the audio player 69 may add or subtract the audio data of different sampling positions to display, or play them in percentage.

Figure 8:
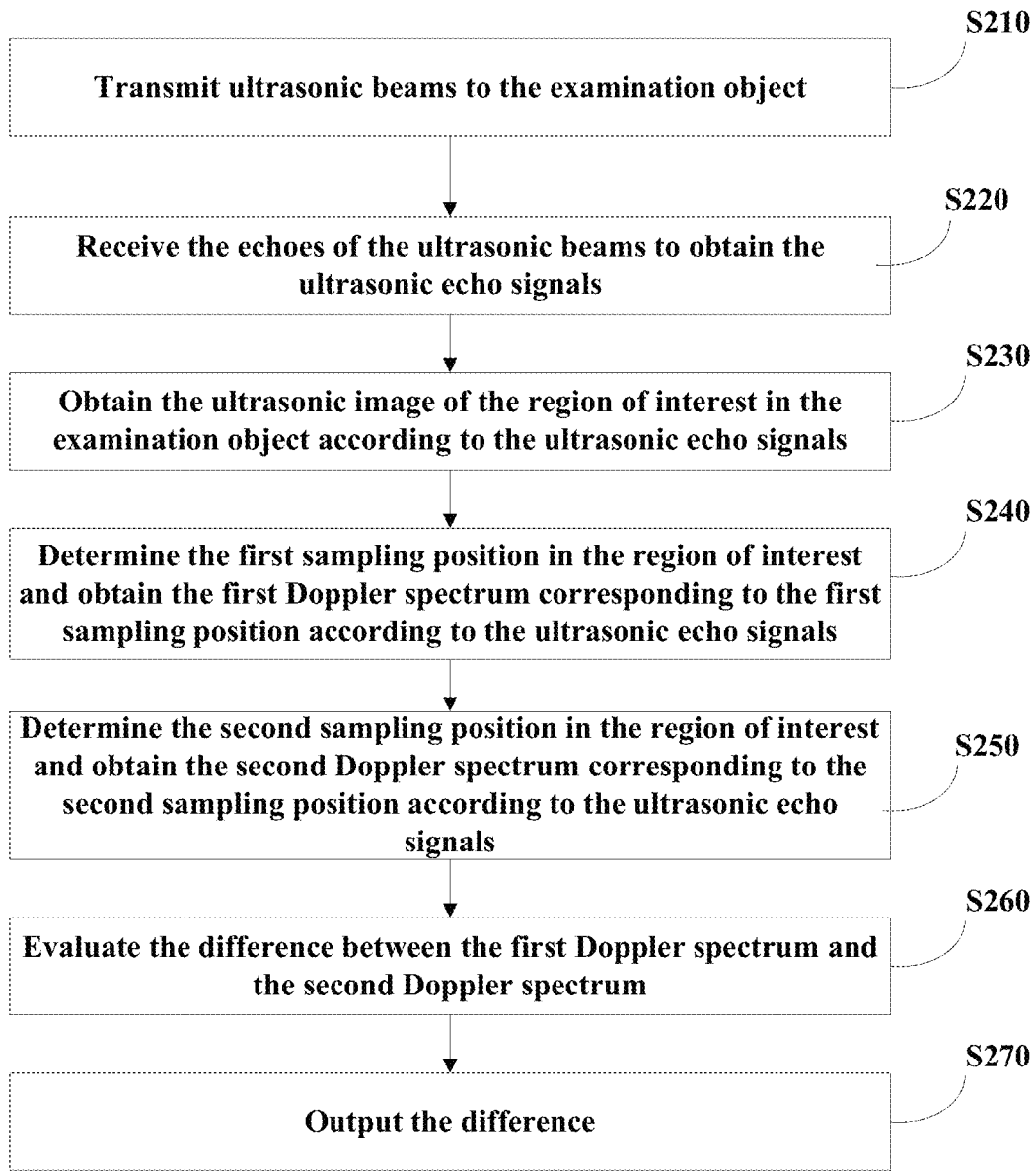
FIG. 8 is a schematic diagram of an embodiment of a new measurement data presentation manner provided by the present disclosure.

Based on the embodiment shown in FIG. 2 and its variant embodiment, a new measurement data presentation method may also be provided in one embodiment, which can present the difference between multiple spectrums to the user and provide more diagnostic reference data. Referring to FIG. 8, the method may include the following steps.

In step S210, the transmitting circuit may transmit the ultrasonic beam to the examination object;

In step S220, the receiving circuit and the beam-former may receive the echoes of the ultrasonic beam to obtain the ultrasonic echo signals;

In step S230, the image processor may obtain the ultrasonic image of the region of interest in the examination object according to the ultrasonic echo signals;

In step S240, the image processor may determine a first sampling position in the region of interest and obtain a first Doppler spectrum corresponding to the first sampling position according to the ultrasonic echo signals;

In step S250, the image processor may determine a second sampling position in the region of interest and obtain a second Doppler spectrum corresponding to the second sampling position according to the ultrasonic echo signals;

In step S260, the image processor may evaluate the difference between the first Doppler spectrum and the second Doppler spectrum;

In step S270, the difference obtained by the evaluation may be output using the display and/or the audio player.

In the present embodiment, the ultrasonic beam may be the non-strongly focused ultrasonic beam or the focused ultrasonic beam. The implementation of the steps 210, 220 and 230 may refer to the description with regard to the steps 110 to 130 above. Steps S240, S250, S260 and S270 may refer to the foregoing descriptions with regard to the steps S140, S150, and S160 about determining the sampling positions in the region of interest or the ultrasonic image and evaluating the difference between the Doppler spectrums, and will not be described here again. The ultrasonic image in this embodiment may include any of the ultrasonic images obtained in the embodiments above, such as the ultrasonic flow state image, the B mode ultrasonic image, etc. Moreover, in one embodiment, the method may further include displaying the first Doppler spectrum and the second Doppler spectrum with the display. In this embodiment, it may also be possible to simultaneously display two Doppler spectrums on the display. In the embodiment above, the difference between the first Doppler spectrum and the second Doppler spectrum may be calculated, and the difference between the different sampling positions can be intuitively obtained through the difference of the spectrums, such that the region in which the change occurs (generally it is possible lesion region or the region that requires special attention) can be found as soon as possible.

Figure 9:
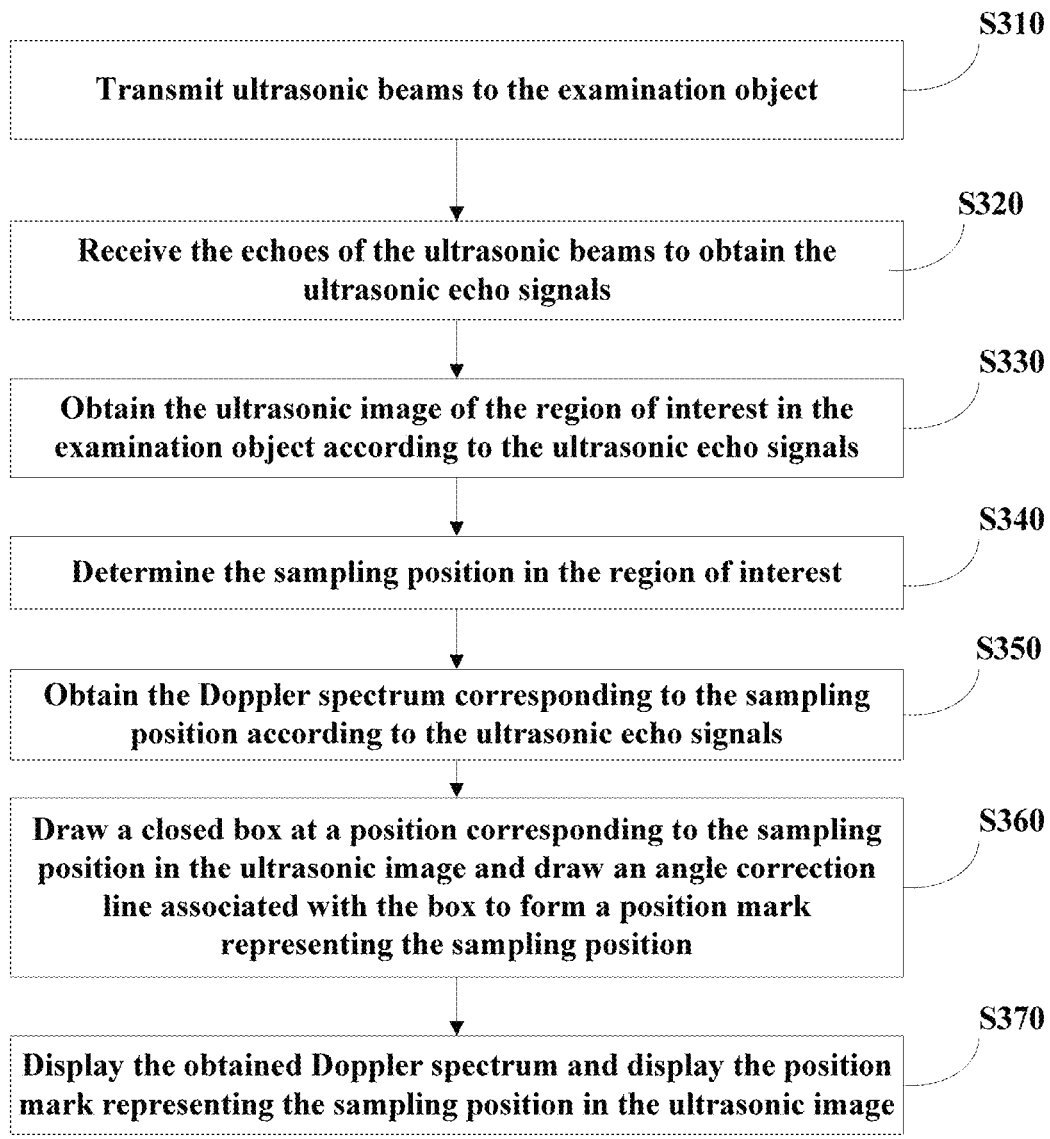
FIG. 9 is a schematic diagram of an embodiment of a new measurement data presentation manner provided by the present disclosure.

Based on the embodiment shown in FIG. 2 and its variant embodiment, a new measurement data presentation method may also be provided in one embodiment of the present disclosure, which can provide distinctive sampling gates to the user and can conveniently cooperate with the displaying of the Doppler spectrums corresponding to multiple sampling positions, thereby providing the user with a more user-friendly operation. Referring to FIG. 9, the method may include the following steps.

In step S310, the transmitting circuit may transmit the ultrasonic beam to the examination object;

In step S320, the receiving circuit and the beam-former may receive the echoes of the ultrasonic beam to obtain the ultrasonic echo signals;

In step S330, the image processor may obtain the ultrasonic image of the region of interest in the examination object according to the ultrasonic echo signals;

In step S340, the image processor may determine the sampling position in the region of interest;

In step S350, the image processor may obtain the Doppler spectrum corresponding to the sampling position according to the ultrasonic echo signals;

In step S360, the image processor may draw a closed box at the position corresponding to the sampling position in the ultrasonic image and draw an angle correction line associated with the box to form the position displaying mark for representing the sampling position;

In step S370, the obtained Doppler spectrum may be displayed by the display, and display the position displaying mark representing the sampling position in the ultrasonic image by the display.

In the present embodiment, the ultrasonic beam may be the non-strongly focused ultrasonic beam or the focused ultrasonic beam. The implementation of the steps 310, 320 and 330 may refer to the related description with regard to the steps 110 to 130 above. The step S340, step S350, step S360 and step S370 may refer to the related descriptions with regard to the steps S140, S150, S160 and S170 about determining the sampling position in the region of interest or the ultrasonic image and the position displaying mark, and will not be described here again. In the embodiments above, by adjusting the box and adjusting the angle correction line, it is possible to achieve more convenient parameter adjustment and data measurement when simultaneously displaying two or more Doppler spectrums. In the present embodiment, the ultrasonic image may include any of the ultrasonic images obtained in the embodiments above, such as the ultrasonic flow state image, the B mode ultrasonic image, and the like.

In the ultrasonic flow spectrum Doppler imaging method and the ultrasonic flow spectrum Doppler imaging system provided in the embodiments of the present disclosure, while displaying the B mode, the C mode, the D mode or the ultrasonic flow state image, the spectral image at any two or more positions in the flow region in the ultrasonic image may also be displayed, such that the user can obtain the diagnosis result intuitively, quickly, accurately and comprehensively, which not only helps to improve the diagnosis efficiency, but also helps to improve the diagnosis accuracy.

Moreover, in some embodiments of the present disclosure, the spectral image may be an original image or a difference image, such that the user can determine more accurately and accurately from the examination object whether there is an abnormality or a lesion or the like. Taking the ultrasonic flow state image being an ultrasonic blood flow projection image as an example, the blood flow velocity vector information and the Doppler spectrum may be calculated based on the same group of ultrasonic echo signals. For example, the blood flow velocity vector information and the Doppler spectrum may be calculated according to the obtained same group of echo signals of the non-strongly focused ultrasonic beams. The methods will also be applicable to other flow replacing the blood flow.

The present disclosure has been described above with reference to specific embodiments. However, the present disclosure will not be limited to the specific embodiments. Those skilled in the art will understand that various modifications, equivalents, changes, etc. may be made to the present disclosure. As long as not departing from the spirit of the present disclosure, they shall all be in the scope of the present disclosure. In addition, the "one embodiment" described above in various places may mean different embodiments, or, all or a part of them may be combined in one embodiment.

The invention claimed is:

1. An ultrasonic flow spectral Doppler imaging method, comprising:
   transmitting an ultrasonic beam to an examination object;
   receiving echoes of the ultrasonic beam to obtain an ultrasonic echo signal:
   obtaining an ultrasonic image of a region of interest in the examination object according to the ultrasonic echo signal;
   determining a first sampling position in the region of interest and obtaining a first Doppler spectrum corresponding to the first sampling position according to the ultrasonic echo signal;
   determining a second sampling position in the region of interest and obtaining a second Doppler spectrum corresponding to the second sampling position according to the ultrasonic echo signal:
   displaying, in a first area of a display, the ultrasonic image with markers of the first and second sampling positions; and
   simultaneously displaying the first Doppler spectrum and the second Doppler spectrum in second and third areas of the display, respectively, wherein first Doppler spectrum and second Doppler spectrum are synchronously displayed along a same time axis, the first Doppler spectrum is assigned with a first color identifier, the second Doppler spectrum is assigned with a second color identifier, a color of the first color identifier different from a color of the second color identifier, the marker of the first sampling position has the same color as that of the first color identifier, and the marker of the second sampling position has the same color as that of the second color identifier.

2. The ultrasonic flow spectral Doppler imaging method of claim 1, further comprising:

extracting a same attribute parameter of the first Doppler spectrum and the second Doppler spectrum; and calculating a difference between the extracted attribute parameters to obtain a difference between the first Doppler spectrum and the second Doppler spectrum.

3. The ultrasonic flow spectral Doppler imaging method of claim 1, wherein, in the step of transmitting the ultrasonic beam to the examination object, the ultrasonic beam is one of a plane ultrasonic beam, a diverged ultrasonic beam and a weakly focused ultrasonic beam, or a combination thereof.

4. The ultrasonic flow spectral Doppler imaging method of claim 1, wherein the ultrasonic image is an ultrasonic flow state image that is obtained by one of:

displaying a flow velocity vector identifier on the ultrasonic image, wherein the flow velocity vector identifier represents a flow velocity vector information;

mapping a trend of a collected flow signal with image grayscale and/or image color information on the ultrasonic image; or displaying a flow velocity vector identifier representing a flow velocity vector information on the ultrasonic image and mapping a trend of a collected flow signal with image grayscale and/or image color information.

5. An ultrasonic flow spectral Doppler imaging system, comprising:

a transmitting circuit that is configured to transmit an ultrasonic beam to an examination object;

a receiving circuit that is configured to receive echoes of the ultrasonic beam to obtain an ultrasonic echo signal:

an image processor that is configured to obtain an ultrasonic image of a region of interest in the examination object according to the ultrasonic echo signal, determine a first sampling position in the region of interest and obtain a first Doppler spectrum corresponding to the first sampling position according to the ultrasonic echo signal, determine a second sampling position in the region of interest and obtain a second Doppler spectrum corresponding to the second sampling position according to the ultrasonic echo signal; and a display having first, second, and third areas, wherein the ultrasonic image is displayed with markers of the first and second sampling position in the first area, and the first Doppler spectrum and second Doppler spectrum are simultaneously displayed in the second and third areas of the display, respectively, wherein first Doppler spectrum and second Doppler spectrum are synchronously displayed along a same time axis, the first Doppler spectrum is assigned with a first color identifier, the second Doppler spectrum is assigned with a second color identifier, a color of the first color identifier different from a color of the second color identifier, the marker of the first sampling position has the same color as that of the first color identifier, and the marker of the second sampling position has the same color as that of the second color identifier.

6. The ultrasonic flow spectral Doppler imaging system of claim 5, wherein the image processor is configured to extract a same attribute parameter of the first Doppler spectrum and the second Doppler spectrum and calculate a difference between the extracted attribute parameters to obtain a difference between the first Doppler spectrum and the second Doppler spectrum.

7. The ultrasonic flow spectral Doppler imaging system of claim 5, wherein the ultrasonic beam is one of a plane ultrasonic beam, a diverged ultrasonic beam and a weakly focused ultrasonic beam, or a combination thereof.

8. The ultrasonic flow spectral Doppler imaging system of claim 5, wherein the ultrasonic image is an ultrasonic flow state image that is obtained by one of:

displaying a flow velocity vector identifier on the ultrasonic image, wherein the flow velocity vector identifier represents a flow velocity vector information;

mapping a trend of a collected flow signal with image grayscale and/or image color information on the ultrasonic image; or displaying a flow velocity vector identifier representing a flow velocity vector information on the ultrasonic image and mapping a trend of a collected flow signal with image grayscale and/or image color information.

\* \* \* \* \*